US008785407B2

(12) United States Patent
Stein et al.

(10) Patent No.: US 8,785,407 B2
(45) Date of Patent: *Jul. 22, 2014

(54) ANTISENSE ANTIVIRAL AGENT AND METHOD FOR TREATING SSRNA VIRAL INFECTION

(75) Inventors: David A. Stein, Corvallis, OR (US);
Douglas E. Skilling, Corvallis, OR (US);
Patrick L. Iversen, Corvallis, OR (US);
Alvin W. Smith, Corvallis, OR (US);
Dwight D. Weller, Corvallis, OR (US)

(73) Assignee: Sarepta Therapeutics, Inc., Corvallis, OR (US)

( * ) Notice: Subject to any disclaimer, the term of this patent is extended or adjusted under 35 U.S.C. 154(b) by 933 days.

This patent is subject to a terminal disclaimer.

(21) Appl. No.: 11/431,968

(22) Filed: May 10, 2006

(65) Prior Publication Data
US 2007/0265214 A1    Nov. 15, 2007

(51) Int. Cl.
*C12N 15/11*    (2006.01)

(52) U.S. Cl.
USPC ............................................ 514/44 A

(58) Field of Classification Search
USPC ............................................ 514/44 A
See application file for complete search history.

(56) References Cited

U.S. PATENT DOCUMENTS

| 5,034,506 A | 7/1991 | Summerton et al. ......... 528/391 |
| 5,142,047 A | 8/1992 | Summerton et al. |
| 5,166,315 A | 11/1992 | Summerton et al. ......... 528/406 |
| 5,185,444 A | 2/1993 | Summerton et al. |
| 5,194,428 A | 3/1993 | Agrawal et al. |
| 5,217,866 A | 6/1993 | Summerton et al. ............ 435/6 |
| 5,495,006 A * | 2/1996 | Climie et al. ............... 536/24.1 |
| 5,506,337 A | 4/1996 | Summerton et al. ......... 528/391 |
| 5,521,063 A | 5/1996 | Summerton et al. ............ 435/6 |
| 5,576,302 A | 11/1996 | Cook et al. |
| 5,580,767 A | 12/1996 | Cowsert et al. |
| 5,698,685 A | 12/1997 | Summerton et al. |
| 5,702,891 A | 12/1997 | Kolberg et al. |
| 5,734,039 A | 3/1998 | Calabretta et al. |
| 5,738,985 A | 4/1998 | Miles et al. |
| 5,749,847 A * | 5/1998 | Zewert et al. ............... 604/501 |
| 5,801,154 A | 9/1998 | Baracchini et al. |
| 5,892,023 A * | 4/1999 | Pirotzky et al. ............. 536/24.5 |
| 5,955,318 A | 9/1999 | Simons et al. |
| 5,985,662 A | 11/1999 | Anderson et al. ............ 435/375 |
| 5,989,904 A | 11/1999 | Das et al. |
| 6,060,456 A | 5/2000 | Arnold et al. |
| 6,133,246 A | 10/2000 | McKay et al. |
| 6,174,868 B1 | 1/2001 | Anderson et al. |
| 6,214,555 B1 | 4/2001 | Leushner et al. |
| 6,228,579 B1 | 5/2001 | Zyskind et al. |
| 6,239,265 B1 | 5/2001 | Cook |
| 6,258,570 B1 | 7/2001 | Glustein et al. |
| 6,306,993 B1 | 10/2001 | Rothbard et al. |
| 6,365,351 B1 | 4/2002 | Iversen |
| 6,365,577 B1 | 4/2002 | Iversen .............................. 4/2 |
| 6,391,542 B1 | 5/2002 | Anderson et al. |
| 6,495,663 B1 | 12/2002 | Rothbard et al. |
| 6,669,951 B2 | 12/2003 | Rothbard et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 6,841,675 B1 | 1/2005 | Schmidt et al. ............... 544/336 |
| 6,881,825 B1 | 4/2005 | Robbins et al. |
| 7,049,431 B2 | 5/2006 | Iversen et al. |
| 7,094,765 B1 | 8/2006 | Iversen et al. |
| 7,115,374 B2 | 10/2006 | Linnen et al. |
| 7,468,418 B2 | 12/2008 | Iversen et al. ................. 530/300 |
| 7,507,196 B2 | 3/2009 | Stein et al. ...................... 514/44 |
| 7,524,829 B2 | 4/2009 | Stein et al. ...................... 514/44 |
| 7,582,615 B2 | 9/2009 | Neuman et al. ................. 514/44 |
| 7,943,762 B2 | 5/2011 | Weller et al. .................... 536/31 |
| 2003/0095953 A1 * | 5/2003 | Cabot et al. ............... 424/93.21 |
| 2003/0166588 A1 * | 9/2003 | Iversen et al. .................. 514/44 |
| 2003/0171311 A1 | 9/2003 | Blatt et al. |
| 2003/0171335 A1 | 9/2003 | Stein et al. |
| 2003/0175767 A1 * | 9/2003 | Davis et al. ....................... 435/6 |
| 2003/0224353 A1 | 12/2003 | Stein et al. |
| 2004/0072239 A1 | 4/2004 | Renaud et al. |
| 2004/0259108 A1 | 12/2004 | Linnen et al. ...................... 12/4 |
| 2004/0265879 A1 | 12/2004 | Iversen et al. .................... 435/6 |
| 2005/0171044 A1 | 8/2005 | Stein et al. ...................... 514/44 |
| 2005/0176661 A1 | 8/2005 | Vaillant et al. |
| 2006/0063150 A1 | 3/2006 | Iversen et al. |

(Continued)

FOREIGN PATENT DOCUMENTS

| WO | WO 98/12312 A1 | 3/1998 |
| WO | 99/29350 | 6/1999 |

(Continued)

OTHER PUBLICATIONS

Agrawal et al. (1988) Proc. Natl. Acad. Sci. 85:7079-7083.*
Deas, T.S., et al., *Journal of Virology* 79(8):4599-4609, (2005).
Jubin, R., et al., *Journal of Virology* 74(22):10430-10437, (2000).
Raviprakash, K., et al., *Journal of Virology* 69(1):69-74, (1995).
Agrawal et al. *Proc Natl Acad Sci U S A.*, 87(4):1401-5 (1990).
Bailey et al., "Cationic oligonucleotides can mediate specific inhibition of gene expression in *Xenopus* oocytes." *Nucleic Acids Res*, 26(21):4860-7 (1998).
Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).
Blommers et al., *Nucleic Acids Res.*, 22(20):4187-94 (1994).
Bonham et al., *Nucleic Acids Res.*, 23(7):1197-203 (1995).

(Continued)

*Primary Examiner* — J. E. Angell
(74) *Attorney, Agent, or Firm* — Seed IP Law Group PLLC

(57) ABSTRACT

The invention provides antisense antiviral compounds and methods of their use in inhibition of growth of viruses of the picornavirus, calicivirus, togavirus and flavivirus families, as in treatment of a viral infection. The antisense antiviral compounds have morpholino subunits linked by uncharged phosphorodiamidate linkages interspersed with cationic phosphorodiamidate linkages.

12 Claims, 8 Drawing Sheets

(56) References Cited

U.S. PATENT DOCUMENTS

| | | | |
|---|---|---|---|
| 2006/0148747 A1 | 7/2006 | Stein et al. | 514/44 |
| 2006/0149046 A1 | 7/2006 | Arar | 7/6 |
| 2006/0269911 A1 | 11/2006 | Iversen et al. | |
| 2007/0004661 A1 | 1/2007 | Stein et al. | 514/44 |
| 2007/0066556 A1 | 3/2007 | Stein et al. | |
| 2007/0129323 A1 | 6/2007 | Stein et al. | |
| 2007/0265214 A1 | 11/2007 | Stein et al. | |
| 2009/0012280 A1 | 1/2009 | Stein et al. | 536/23.1 |
| 2009/0082547 A1 | 3/2009 | Iversen et al. | 530/322 |
| 2009/0088562 A1 | 4/2009 | Weller et al. | 536/24.5 |
| 2009/0099066 A1 | 4/2009 | Moulton et al. | 514/7 |
| 2009/0186847 A1 | 7/2009 | Stein et al. | 514/44 |
| 2009/0186848 A1 | 7/2009 | Stein et al. | 514/44 |
| 2009/0186849 A1 | 7/2009 | Stein et al. | 514/44 |
| 2010/0063133 A1 | 3/2010 | Neuman et al. | 514/44 A |

FOREIGN PATENT DOCUMENTS

| | | |
|---|---|---|
| WO | WO01/49775 | 7/2001 |
| WO | WO 02/026968 A1 | 4/2002 |
| WO | WO02/068637 A2 | 9/2002 |
| WO | WO 02/068637 A2 | 9/2002 |
| WO | WO03/033657 A2 | 4/2003 |
| WO | WO2005/007805 A2 | 1/2005 |
| WO | WO2005/007805 A3 | 1/2005 |
| WO | WO2005/013905 A2 | 2/2005 |
| WO | WO2005/013905 A3 | 2/2005 |
| WO | WO 2005/030800 A1 | 4/2005 |
| WO | 2005/065268 | 7/2005 |
| WO | WO 2006/047683 A2 | 4/2006 |
| WO | 2006/050414 | 5/2006 |
| WO | 2007/030576 | 3/2007 |
| WO | 2007/030691 | 3/2007 |
| WO | 2007/103529 | 9/2007 |

OTHER PUBLICATIONS

Boudvillain et al., *Biochemistry* 36(10):2925-31 (1997).
Branch, Andrea D., *TIBS*, 23:45-50 (1998).
Clarke et al., *J. Infect. Diseases*, 181:S309-S316 (2000).
Corey et al., Morpgolino Antisnese Oligonucleotides: Tools for Investigating Vertebrate Development, Genome Biology, 2(5):1015.1-1015.3 (2001).
Cross et al., "Solution structure of an RNAxDNA hybrid duplex containing a 3'-thioformacetal linker and an RNA A-tract." *Biochemistry*, 36(14): 4096-107 (1997).
Dagle et al., "Targeted elimination of zygotic messages in *Xenopus laevis* embryos by modified oligonucleotides possessing terminal cationic linkages", *Nucleic Acids Res.*, 28(10): 2153-7 (2000).
Ding, D., et al., *Nucleic Acids Res* 24(2):354-60, (1996).
Felgner et al., *PNAS*, 84(21): 7413-7 (1987).
Gait et al., *J. Chem. Soc.*, 0(14):1684-1686 (1974).
Gee et al., *Antisense Nucleic Acid Drug Dev* 8(2):103-11 (1998).
Genbank Accession No. AF304460.
Green et al., *J. Am. Coll. Surg.*, 191:93-105 (2000).
Hanecak et al., *Journal of Virology*, 70(8):5203-5212 (1996).
Holland et al., Emerging Virus, Morse, S.S., Ed., Oxford University Press, New York and Oxford pp. 203-218 (1993).
Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).
Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901 (2000).
Micklefield, J., "Backbone modification of nucleic acids: synthesis, structure and therapeutic applications." *Curr Med Chem*, 8(10):1157-79 (2001).
Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.
Moulton, H. M., M. H. Nelson, et al., *Bioconjug Chem* 15(2): 290-9 (2004).
National Center for Biotechnology Information Report No. NC_002645 from NCBI Genome Database (2001).
National Center for Biotechnology Information Report No. AY274119 from NCBI Genome Database (2003).
National Center for Biotechnology Information Report No. AF029248 from NCBI Genome Database (2000).
Nelson et al., "Arginine-rich peptide conjugation to morpholino oligomers: effects on antisense activity and specificity." *Bioconjug Chem.*, 16(4): 959-66 (2005).
O'Ryan et al., in: *Spector S, Lancz G*, Eds., Clinical Virology Manual, New York, Elsevier Science pp. 361-396 (1992).
Orr et al., *Current Opinion in Molecular Therapeuctics*, Current Drugs, 2(3):325-331 (2000).
Partridge et al., Antisense Nucleic Acid Drug Development, 6(3):169-175 (1996).
Sankar e al., *European Journal of Biochemistry*, 184(1):39-45 (1989).
Smith et al., *Emerg. Inf. Dis.*, 4:13-20 (1998).
Smith et al., *Current Opinion Molecular Therapeutcis*, 4(2):177-184 (2002).
Stein, D., et al., *Antisense Nucleic Acid Drug Dev.*, 7(3):151-7, (1997).
Stein et al., *Antisense Nucleic Acid Drug Development*, 11(5):317-325 (2001).
Summerton et al., *Antisense & Nucleic Acid Drug Development*, 7:63-70 (1997).
Summerton et al., *Biochim et. Biophys. ACTA*, 1489:141-158 (1999).
Summerton, J. and D. Weller, "Morpholino antisense oligomers: design, preparation, and properties.", *Antisense Nucleic Acid Drug Dev.*, 7(3): 187-95 (1997).
Thiel et al., *Journal of General Virology*, 82:1273-1281 (2001).
Toulme et al., Targeting RNA structures by antisense oligonucleotides. *Biochimie*, 78(7): 663-73 (1996).
Wages et al., *Biotechniques*, 23:1116-1121 (1997).
Wang et al., *Antimicrobial Agents Chemotherapy*, 45(4):1043-1052 (2001).
Wei et al., *Nucleic Acids Res.*, 28:3065-3074 (2000).
Wu et al., *J. Biol. Chem.*, 267:12436-12439 (1992).
Xu et al., *Revue Scientifique Technique*, Office of International des Epizooties 10:2393-2408 (1991).
Zhang et al., *Antimicrobial Agents Chemotherapy*, 43(2):347-353 (1999).
Lopez De Quinto S. et al., *Virology*, 255(2):324-336 (1999).
Banerjee, R. and A. Dasgupta, "Interaction of picornavirus 2C polypeptide with the viral negative-strand RNA." *J Gen Virol* 82(Pt 11):2621-7 (2001).
Banerjee, R. and A. Dasgupta, "Specific interaction of hepatitis C virus protease/helicase NS3 with the 3'-terminal sequences of viral positive- and negative-strand RNA." J Virol 75(4):1708-21 (2001).
Banerjee, R., A. Echeverri, et al., "Poliovirus-encoded 2C polypeptide specifically binds to the 3'-terminal sequences of viral negative-strand RNA." J Virol 71(12):9570-8 (1997).
Banerjee, R., W. Tsai, et al., "Interaction of poliovirus-encoded 2C/2BC polypeptides with the 3' terminus negative-strand cloverleaf requires an intact stem-loop b." *Virology*, 280(1): 41-51 (2001).
Egholm et al., "PNA hybridizes to complementary oligonucleotides obeying the Watson-Crick hydrogen-bonding rules." *Nature*, 365(6446):566-8 (1993).
Jaeger, J.A., et al., *Proc. Natl. Acad. Sci. USA*, 86:7706-7710, (1989).
Jubin, R., et al., *Journal of Virology*, 74(22):10430-10437, (2000).
Markoff, L., *Adv. Virus Res.*, 59:177-228 (2003).
Moulton et al., Abstracts of Papers American Chemical Society National Meeting 226 (1-2): Biol 75 (Sep. 7-11, 2003).
Neuman, B.W., et al., *Journal of Virology*, 78(11):5891-5899 (2004).
Pardigon, N. and J. H. Strauss, "Cellular proteins bind to the 3' end of Sindbis virus minus-strand RNA." *J Virol.*, 66(2):1007-15 (1992).

(56) References Cited

OTHER PUBLICATIONS

Pardigon, N., E. Lenches, et al., "Multiple binding sites for cellular proteins in the 3' end of Sindbis alphavirus minus-sense RNA." *J Virol.*, 67(8): 5003-11 (1993).
Paul, A. V., Possible unifying mechanism of picornavirus genome replication. *Molecular Biology of Picornaviruses*. B. L. Semier and E. Wimmer. Washington, DC, ASM Press:227-246 (2002).
Raviprakash, K., et al., *Journal of Virology*, 69(1):69-74, (1995).
Roehl, H. H. and B. L. Semler, "Poliovirus infection enhances the formation of two ribonucleoprotein complexes at the 3' end of viral negative-strand RNA." *J Virol.*, 69(5):2954-61 (1995).
Roehl, H. H., T. B. Parsley, et al., "Processing of a cellular polypeptide by 3CD proteinase is required for poliovirus ribonucleoprotein complex formation." *J Virol.* 71(1):578-85 (1997).
Rothbard et al., *J. Med. Chem.*, 45:3612-3618 (2002).
Siprashvili, Z., et al., *Human Gene Therapy*, 14:1225-1233, (2003).
Smith, R.M. and Wu, G.Y., *Journal of Viral Hepatitis*, 11:115-123 (2004).
Xu, W. Y. (1991). "Viral haemorrhagic disease of rabbits in the People's Republic of China: epidemiology and virus characterisation." *Rev Sci Tech*, 10(2):393-408.
Zuker, M., *Nucleic Acids Res.*, 31(13):3406-3415 (2003).
Brasey et al., "The leader of human immunodeficiency virus type 1 genomic RNA harbors an internal ribosome entry segment that is active during the G2/M phase of the cell cycle", *Journal of Virology*, 77(7):3939-3949 (2003).
Johannes et al., "Identification of eukaryotic mRNAs that are translated at reduced cap binding complex eIF4F concentrations using a cDNA microarray", *Proc. Natl. Acad. Sci. USA*, 96(23):13118-13123 (1999).
Liu et al., "Structural and functional analysis of the 5' untranslated region of coxsackievirus B3 RNA: In vivo translational and infectivity studies of full-length mutants", *Virology*, 265:206-217 (1999).
McCaffrey et al., "A potent and specific morpholino antisense inhibitor of hepatitis C translation in mice", *Hepatology*, 38(2):503-508 (2003).
Fischer, P.M., "Cellular uptake mechanisms and potential therapeutic utility of peptidic cell delivery vectors: progress 2001-2006" Published online 2006 in Wiley Interscience, www.interscience.wiley.com pp. 1-41 (2006).
Shengqi et al., "Synthesis of Antisense Phosphothioate Oligodeoxynucleotides of Dengue Fever Virus and Their Anti-Viral Activity", *Progress in Biochemistry and Biophsics*, 24:64-68 (English Translation) (1997). 4.
Wilson et al., "Naturally occurring dicistronic cricket paralysis virus RNA is regulated by two internal ribosome entry sites", *Mol. Cell. Biol.*, 20(14):4990-4999 (2000).
Wu, G.Y. and Wu, C.H., "Receptor-mediated in vitro gene transformation by a soluble DNA carrier system", *J. Biol. Chem.* 262(10):4429-4432 (1987).
Yuan et al., "A phosphorothioate antisense oligodeoxynucleotide specifically inhibits coxsackievirus B3 replication in cardiomyocytes and mouse hearts", *Labotratory Investigation*, 84:703-714 (2004).
Agrawal et al., "Antisense Therapeutics: Is it as Simple as Complementary Bse Recognition?", *Molecular Medicine Today*, 6:72-81 (2000).
Basler et al., "The Ebola virus VP35 protein functions as a type I IFN antagonist", *Proc. Natl. Acad. Sci. U.S.A.*, 97(22):12289-12294 (2000).
Chirilla et al., "The use of synthetic polymers for delivery of therapeutic antisense oligodeoxynucleotides", *Biomaterials*, 23(2):321-342 (2002).
Cox, N.J. and Subbaro, K., "Influenza", *Lancet*, 354(9186):1277-1282 (1999).
Cox, N.J. and Subbaro, K., "Global Epidemiology of Influenza: Past and Present", *Annual review Medicine*, 51:407-421 (2000).
International Search Report and Written Opinion for PCT/US2007/011435, search report dated, Sep. 29, 2008, 10 pages (2008).

Crooke, S. T., Antisense Drug Technology: Principles, Strategies, and Applications. New York, Marcel Dekker, S. Crooke Ed Springer pp. 1-50 (1999).
Gilbert et al., "Sieve analysis: methods for assessing from vaccine trial data how vaccine efficacy varies with genotypic and phenotypic pathogen variation", Journal of *Clinical Epidemiology*, 54(1):68-85 (2001).
Hudziak et al., "Resistance of morpholino phosphorodiamidate oligomers to enzymatic degradation", *Antisnese & Nucleic Acid Drug Developement.*, 6:267-272 (1996).
Jen et al., "Suppression of Gene Expression by Targeted Disruption of Messenger RNA:Available Options and Current Strategies", *Stem Cells*, 18:307-319 (2000).
Palu et al., "In pursuit of new developments for gene therapy of human diseases", *Journal of Biotechnology*, 68:1-13 (1999).
Scanlon, K.I, "Anti-genes: siRNA, ribozymes and antisense", *Current Pharmaceutical Biotechnology*, 5(5):415-420 (2004).
Taylor et al., "Antisense oligonucleotides: a systematic high-throughput approach to target validation and gene function determination", *Drug Discovery Today*, 4:562-567 (1999).
Williams, A.S. et al., "A single intra-articular injection of liposomally conjugated methotrexate suppresses joint inflammation in rat antigen-induced arthritis", *British Journal of Rheumatology*, 35(8):719-724 (1996).
Zollinger, W.D. and Moran, E., "Meningococcal vaccines—present and future", *Transactions of Royal Soc of Tropical Medicine and Hygiene*, 85(Supp. 1):37-43 (1991).
Arora and Iversen, "Redirection of drug metabolism using antisense technology", *Curr. Opin Mol. Ther.*, 3(3):249-257 (2001).
Borio, L. et al., "Hemorrhagic fever viruses as biological weapons: medical and public health management", *The Journal of the American Medical Association*, 287(18):2391-2405 (2002).
Bray, M. et al., "A mouse model for evaluation of prophylaxis and therapy of Ebola hemorrhagic fever", *The Journal of Infectious Diseases*, 178(3):651-661 (1998).
Burnett, J.C. et al., "The evolving field of biodefence: therapeutic developments and diagnostics", *Natural Review Drug Discovery*, 4:281-297 (2005).
European Search Report for European application 05796604.6, search report dated, Jan. 5, 2009, 8 pages (2009).
Connolly, B.M. et al., "Pathogenesis of experimental Ebola virus infection in guinea pigs", *The Journal of Infectious Diseases*, 179(Suppl. 1):S203-S217 (1999).
Feldmann, H. et al., "Ebola Virus: from Discovery to Vaccine", *Nature Review Immunology*, 3(8):677-685 (2003).
Feldman, H. et al., *Current Topics in Microbiology and Immunology*, Classsification, Structure, and Replication of Filoviruses, pp. 1-21 (1999).
Feldman, H. et al., "Molecular Biology and Evolution of Filoviruses", *Arch. Virol.*, 7(Suppl.):81-100 (1993).
Freier, S.M., in Antisense Drug Technology: Principles, Strategies, and Applications, Chapter 5, pp. 107-118 (2001).
Geisbert, T.W. and Hensley, L.E.,"Ebola virus: new insights into disease aetiopathology and possible therapeutic interventions", *Expert Reviews in Molecular Medicine*, 6(20):1-24 (2004).
Geisbert, T.W. et al.,"Treatment of Ebola virus infection with a recombinant inhibitor of factor Vlla/tissue factor: a study in rhesus monkeys", *The Lancet*, 362(9400):1953-1958 (2003).
Jahrling, P.B. et al., "Evaluation of immune globulin and recombinant interferon-alpha2b for treatment of experimental Ebola virus infections", *The Journal of Infectious Diseases*, 179(Suppl 1):S224-S234 (1999).
Miranda, M.B. et al., "Differential activation of apoptosis regulatory pathways during monocytic vs granulocytic differentiation: a requirement for Bcl-X(L)and XIAP in the prolonged survival of monocytic cells", *Journal of the Leukemia Society of America*, 17(2):1157-79 (2001).
Peters, C.J. and Ledue, J.W., "An introduction to Ebola: the virus and the disease", *The Journal of Infectious Diseases*, 179(Suppl 1):ix-xvi (1999).
Sanchez, A. et al., "Sequence analysis of the Ebola virus genome: organization, genetic elements, and comparison with the genome of Marburg virus", *Virus Research*, 29(3):215-240 (1993).

(56) References Cited

OTHER PUBLICATIONS

Shabbits, J.A. et al., "Tumor chemosensitization strategies based on apoptosis manipulations", *Molecular Cancer Therapeuctics*, 2(8):805-813 (2003).
Vlasov et al., "Inhibition of the Influenza Virus M Protein mRNA Transaltion in vitro with Complementary Oligonucleotides", *Nucleosides & Nucleotides*, 10(1-3):649-650 (1991).
Warfield, K.I. et al., "Role of natural killer cells in innate protection against lethal ebola virus infection", *The Journal of Experimental Medicine*, 200(2):169-179 (2004).
Callahan, P.L. et al. "Molecular cloning and complete sequence determination of RNA genome of human rhinovirus type 14", *Proc. Natl. Acad. Sci. U.S.A.*, 82(3):732-736 (1985).
Crooke, R.M. et al. "In vitro toxicological evaluation of ISIS 1082, a phosphorothioate oligonucleotide inhibitor of herpes simplex virus", *Antimicrobial Agents and Chemotherapy*, 36(3):527-532 (1992).
Faria, M. et al., "Phosphoramidate oligonucleotides as potent antisense molecules in cells and in vivo", *Nature Biotechnology*, 19(1):40-44 (2001).
Kinney et al., "Inhibition of dengue virus serotypes 1 to 4 in vero cell cultures with morpholino oligomers", *Journal of Virology*, 79:5116-5128 (2005).
Lee, W-M. et al., "Complete sequence of the RNA genome of human rhinovirus 16, a clinically useful common cold virus belonging to the ICAM-1 receptor group", *Virus Genes*, 9(2):177-184 (1994).
Mizuta, T. et al., "Antisense oligonucleotides directed against the viral RNA polymerase gene enhance survival of mice infected with influenza A", *Nature Biotechnology*, 17(6):583-587 (1999).
NCBI Genbank Nucleotide Accession No. AF091736, VESV-like calicivirus strain Pan-1, complete genome, 5 pages (1998).
NCBI Genbank Nucleotide Accession No. AF169005, Hepatitis C virus subtype 2a isolate NDM59, complete genome, 5 pages (1999).
Robaczewska, M. et al., "Inhibition of hepadnaviral replication by polyethylenimine-based intravenous delivery of antisense phosphodiester oligodeoxynucleotides to the liver.", *Nature Publishingucleic Acids Res.*, 31(13):3406-15 (2003).
Sosnovtsev, S. and Green K.Y, "RNA transcripts derived from a cloned full-length the feline calicivirus genome do not require VpG for infectivity", *Virology*, 210:383-390 (1995).
Alt et al., "Specific inhibition of hepatitis C viral gene expression by antisense phosphorothioate oligodeoxynucleotides" Hepatology 22(3): 707-717, 1995.
Ghosh et al., "Intracellular Delivery Strategies for Antisense Phosphorodiamidate Morpholino Oligomers" Antisense & Nucleic Acid Drug Development 10: 263-274, 2000.
Hames et al., *Nucleic Acid Hybridisation*, IRL Press, Oxford, 1985, 245 pages, 107-108.
International Search Report, for Application No. PCT/US2002/032868, mailed Nov. 25, 2003, 6 pages.
International Search Report, for Application No. PCT/US2004/025335, mailed Apr. 27, 2005, 7 pages.
International Search Report, for Application No. PCT/US2004/043341, mailed Nov. 18, 2005, 4 pages.
International Search Report, for Application No. PCT/US2005/038780, mailed Jul. 12, 2006, 5 pages.
International Search Report, for Application No. PCT/US2005/039607, mailed Aug. 29, 2007, 4 pages.
International Search Report, for Application No. PCT/US2006/034786, mailed Apr. 24, 2007, 2 pages.
International Search Report, for Application No. PCT/US2006/034986, mailed Apr. 24, 2007, 2 pages.
International Search Report, for Application No. PCT/US2007/005977, mailed Oct. 23, 2007, 2 pages.
Iversen et al., "Antisense Antiviral Compounds and Methods for Treating a Filovirus Infection" U.S. Appl. No. 12/853,180, filed Aug. 9, 2010, 99 pages.
Iversen, "Antisense Antiviral Compound and Method for Treating Influenza Viral Infection" U.S. Appl. No. 61/261,278, filed Nov. 13, 2009, 105 pages.
Iversen, "Antisense Antiviral Compound and Method for Treating Influenza Viral Infection" U.S. Appl. No. 61/292,056, filed Jan. 4, 2010.
Iversen, "Phosphorodiamidate morpholino oligomers: Favorable properties for sequence-specific gene inactivation" Current Opinion in Molecular Therapeutics 3(3): 235-238, 2001.
Leyssen et al., "Perspectives for the Treatment of Infections with *Flaviviridae*" Clinical Microbiology Reviews 13(1): 67-82, 2000.
Schuster et al., "Secondary Structure of the 3' Terminus of Hepatitis C Virus Minus-Strand RNA" Journal of Virology 76(16): 8058-8068, 2002.
Stein et al., "Oligonucleotide Compound and Method for Treating Nidovirus Infections" U.S. Appl. No. 11/432,155, filed May 10, 2006, 71 pages.
Vickers et al., "Effects of RNA secondary structure on cellular antisense activity" Nucleic Acids Research 28(6): 1340-1341, 2000.
Wakita et al., "Antiviral Effects of Antisense RNA on Hepatitis C Virus RNA Translation and Expression" Journal of Medical Virology 57: 217-222, 1999.
Declaration of Patrick L. Iversen, Ph.D. Under 37 C.F.R. § 1.132, executed on Mar. 17, 2011.
Mitev et al., "Inhibition of Intracellular Growth of *Salmonella enterica* Serovar Typhimurium in Tissue Culture by Antisense Peptide-Phosphorodiamidate Morpholino Oligomer," *Antimicrobial Agents and Chemotherapy* 53(9):3700-3704, 2009.
Moulton et al., "HIV Tat Peptide Enhances Cellular Delivery of Antisense Morpholino Oligomers," *Antisense and Nucleic Acid Drug Development* 13:31-43, 2003.
Neuman et al., "Antisense Morpholino-Oligomers Directed against the 5' End of the Genome Inhibit Coronavirus Proliferation and Growth," *Journal of Virology* 78(11):5891-5899, 2004.
Warren et al., "Advanced antisense therapies for postexposure protection against lethal filovirus infections," *Nature Medcine* 16(9):991-994, 2010.

\* cited by examiner

ANTISENSE ANTIVIRAL AGENT AND METHOD FOR TREATING SSRNA VIRAL INFECTION

FIELD OF THE INVENTION

This invention relates to antisense oligomers for use in treating a picornavirus, calicivirus, togavirus or flavivirus infection, antiviral treatment methods employing the oligomers, and methods for monitoring binding of antisense oligomers to a viral genome target site.

REFERENCES

Agrawal, S. et al., *Proc. Natl. Acad. Sci. USA* 87(4):1401-5 (1990).
Alt, M. et al., *Hepatology* 22(3):707-17 (1995).
Alvarez-Salas, L. et al., *Antisense Nucleic Acid Drug Dev.* 9:441-450 (1999).
Aurelian, L. et al., *Antisense Nucleic Acid Drug Dev.* 10:77-85 (2000).
Bloomers, M., *Nuc Acids Res,* 22(20):4187 (1994).
Bonham, M. A. et al, *Nucleic Acids Res.* 23(7):1197-1203 (1995).
Boudvillain, M. et al, *Biochemistry* 36(10):2925-31 (1997).
Clarke, G. E., and Lambden, P., *J. Infect. Dis.* 181, S309-316 (2000).
Cottral, G. E., in: *Manual of Standard Methods for Veterinary Microbiology*, Eds., Cornell University Press, Ithica, N.Y. pp. 60-93.
Cross, V. et al, *Biochem* 36:4096 (1997).
Dagle et al, *Nuc Acids Res.* 28(10):2153 (2000).
Ding, D. et al, *Nuc Acids Res.* 24(2):354 (1996).
Felgner et al, *Proc. Nat. Acad. Sci. USA* 84:7413 (1987).
Gait, M. J.; et al, *J. Chem. Soc. Perkin I*, 1684-1686 (1974).
Gee, J. E. et al, *Antisense & Nucleic Acid Drug Dev.* 8:103-111 (1998).
Green, K. et al, *J. Am. Coll. Surg.* 191:93-105 (2000).
Gutierrez, A. et al, *Antiviral Research* 22(1):1-13 (1993).
Hanecak, R. et al, *Journal of Virology* 70(8): 5203-12 (1996).
Holland, J. in: *Emerging Virus*, Morse, S. S., Ed., Oxford University Press, New York and Oxford pp. 203-218 (1993).
Kusunoki, A. et al., *Nucleosides Nucleotides Nucleic Acids* 19:1709-1719 (2000).
Lesnikowski, Z. J. et al., *Nucleic Acids Research* 18(8): 2109-15 (Apr. 25, 1990).
Matteucci, M. *Tetrahedron Lett.* 31:2385-2388 (1990).
McElroy, E. B. et al., *Bioorg. Med. Chem. Lett.* 4:1071 (1994).
Mertes, M. P. et al., *J. Med. Chem.* 12:154-157 (1969).
Miller, P. S. et al., in: *Antisense Research Applications*, Crooke, S. T. and Lebleu, B., Eds., Boca Raton, CRC Press pp. 189 (1993).
Mizuta, T. et al., *Nature Biotechnology* 17:583-587 (1999).
Mohan, V. et al., *Tetrahedron* 51:8655 (1995).
Murray, R. et al., in: *Medical Microbiology* (Third Edition) St. Louis, Mo., Mosby Press pp. 542-543 (1998).
O'Ryan, M. et al., in: *Spector S, Lancz G*, Eds., Clinical Virology Manual, New York, Elsevier Science pp. 361-196 (1992).
Robbins, I. et al., *Methods in Enzymology* 313:189-203 (1999).
Roughton, A. L. et al., *J. Am. Chem. Soc.* 117:7249 (1995).
Smith, A. et al., *Emerg. Inf. Dis.* 4:13-20 (1998a).
Smith A. et al., *Clin. Inf. Dis.* 26:43-40 (1998b).
Stein, C. et al., *Pharmacol & Therapeutics*, 85:231 (2000).
Toulme, J. J. et al., *Biochimie* 78(7):663-73 (1996).
Vasseur, J. J. et al., *J. Am. Chem. Soc.* 114:4006 (1992).
Wei, X. et al., *Nucleic Acids Res.* 28:3065-3074 (2000).
Wu, G. et al., *J. Biol. Chem.* 267:12436-12439 (1992).
Xu, W., *Revue Scientifique et Technique*, Office of International des Epizooties 10:2393-2408 (1991).

BACKGROUND OF THE INVENTION

RNA viruses cause many diseases in wildlife, domestic animals and humans. These viruses are genetically and antigenically diverse, exhibiting broad tissue tropisms and a wide pathogenic potential. The incubation periods of some of the most pathogenic viruses, e.g. the caliciviruses, are very short. Viral replication and expression of virulence factors may overwhelm early defense mechanisms (Xu, 1991) and cause acute and severe symptoms.

There are no specific treatment regimes for many viral infections. The infection may be serotype specific and natural immunity is often brief or absent (Murray et al., 1998). Immunization against these virulent viruses is impractical because of the diverse serotypes. RNA virus replicative processes lack effective genetic repair mechanisms, and current estimates of RNA virus replicative error rates are such that each genomic replication can be expected to produce one to ten errors, thus generating a high number of variants (Hollan, 1993). Often, the serotypes show no cross protection, such that infection with any one serotype does not protect against infection with another. For example, vaccines against the vesivirus genus of the caliciviruses would have to provide protection against over 40 different neutralizing serotypes (Smith et al., 1998a), and vaccines for the other genera of the *Caliciviridae* are expected to have the same limitations.

Antisense agents have been proposed for treating various types of viral infection. In general, the specific proposals to date can be classified according to the type of virus targeted, the viral-genome target, and the type of oligonucleotide backbone employed in the antisense compound. Among the viruses that have been targeted are vesicular stomatitis virus (Robbins and Lebleu, 1999), influenza virus (Mizuta et al., 1999), hepatitis B virus (Wu and Wu, 1992), human papilloma virus (Alvarez-Salas et al, 1999), herpes simplex virus (Aurelian and Smith, 2000), HIV (Kusunoki et al., Wei et al, 2000) and foot-and-mouth disease virus (Gutierrez et al, 1993). Viral genome targets that have been proposed include the IE-2 gene of cytomegalovirus (Green et al, 2000), a stem-loop structure at the 5' non-coding region, the translation initiation codon, a core protein coding sequence of the hepatitis C virus, and the second functional initiator AUG of the foot-and-mouth disease virus (Hanecak et al, 1996; Alt et al, 1995; Gutierrez et al, 1993). Finally, a wide variety of antisense backbone structures have been proposed, including the negatively charged phosphorothioate (PSO) backbone oligomers, particularly the phosphorothioate oligodeoxynucleotides (Hanecak et al, 1996; Alt et al, 1995; Gutierrez et al, 1993) and uniformly modified 2'-methoxyethoxy phosphodiester oligonucleotide (Hanecak et al, 1996).

Discovery and development generally involves demonstration of antiviral activity in cell culture. A compilation of antiviral experiments in cell culture is provided in Table 1 below.

TABLE 1

In vitro Antiviral Antisense Studies

| Virus | Reference |
|---|---|
| Herpes Simplex | Gao et al. (1989) J. Biol. Chem. 264: 11,521 |
| Herpes Simplex | Hoke et al. (1991) Nucl. Acids Res. 19: 5743 |
| Herpes Simplex 1 | Smith et al. (1986) Proc. Natl. Acad Sci 83: 2787 |
| HIV-tat | Stevenson & Iversen (1989) J. Gen. Virol. 70: 2673 |
| HIV-aptamer | Matsukura et al. (1987) Proc. Natl. Acad Sci 84: 7706 |
| HIV-rev | Matsukura et al. (1989) Proc. Natl. Acad Sci 86: 4244 |
| HIV-gag | Agrawal et al. (1989) Proc. Natl. Acad Sci 86: 7790 |
| HIV-LTR TAR element | Vickers et al. (1991) Nucl. Acids Res. 19: 3359 |
| VSV | Agris et al. (1986) Biochemistry 25: 6268 |
| VSV-N protein | Lamaitre et al. (1987) Proc. Natl. Acad Sci 84: 1987 |
| HPV-E2 | Cowsert et al. (1993) Antimic. Agent Chemo. 37: |
| HBV surface gene | Goodarzi et al. (1990) J. Gen Virol. 71: 3021 |
| HBV | Wu & Wu (1992) J Biol Chem 267: 12,436-12,439 |
| SV40 | Graessmann et al. (1991) Nucl. Acids Res. 19: 53 |
| Influenza | Kabanov et al. (1990) FEBS Lett. 259: 327 |
| Influenza | Leiter et al. (1990) Proc. Natl. Acad Sci 87: 3430 |
| Rous Sarcoma Virus | Zamecnik & Stephenson (1978) Proc. Natl. Acad Sci 75: 280 |
| CMV immed. early RNA | Anderson et al. (1996) Antimic. Agent Chemo. 40: 2004 |

Clinical trials have been initiated for antisense therapeutics targeting HIV, HPV, CMV and HCV (Table 2 below), all using phosphorothioate-linked oligonucleotides. As seen, the clinical trial experience to date indicates some failures, although antisense against CMV infection (ISIS2922) has been approved by the FDA, making this the only antisense agent approved by the FDA to date.

TABLE 2

Clinical Trials with Antisense for Antiviral Therapy

| Name | Company | Virus | Status |
|---|---|---|---|
| GEM91 | Hybridon | HIV-gag | 250 pts. Discont. 1997 |
| ISIS2105 | ISIS | HPV (6&11) | 400 pts. Fail phase III |
| ISIS2922 | ISIS | CMV-IE2 | HIV retinitis approved |
| GEM132 | Hybridon | CMV | Phase I |
| ISIS14803 | ISIS | HCV | Phase I |

The initial optimism towards antisense approaches to effective antiviral therapeutics has been blunted. Many of the effective antisense strategies employed in cell culture models (e.g. those in Table 1) have not successfully proceeded to clinical trials. The slow progress is due in part to the lack of robust cell culture models. For example, the HIV isolates that infect cultured cells do not generally reflect those found in the infected population, and the cell culture models do not integrate the roles of the multiple cell types infected. This problem is compounded by the lack of appropriate pre-clinical animal models for the full exploitation of viral gene expression and replication in vivo. Again, in the case of HIV, the human virus either does not infect animals, or, when primates are infected, they do not develop pathology similar to that seen in humans. The risk in developing antisense antiviral agents without robust culture models and appropriate animal models is great.

Thus, there remains a need for an effective antiviral therapy in several virus families, including small, single-stranded, positive-sense RNA viruses in the picornavirus, calicivirus, togavirus and flavivirus families. To meet this need, an antisense agent must be substantially stable against nuclease degradation, able to be taken up readily by virus-infected host cells following compound administration, and targeted against an effective region of the viral genome, that is, able to shut down viral replication.

SUMMARY OF THE INVENTION

In one aspect, the invention provides an antiviral compound directed against an RNA virus from the picornavirus, calicivirus, togavirus or flavivirus families having a single-stranded, positive sense genome of less than 12 kb and a first open reading frame that encodes a polyprotein containing multiple functional proteins. The antiviral compound comprises an oligomer or oligonucleotide compound having a sequence of 12 to 40 morpholino subunits (a) with a targeting base sequence that is substantially complementary to a viral target sequence of at least 12 bases that spans the translation initiation region of said virus first open reading frame, and (b) that are linked by uncharged phosphorodiamidate linkages interspersed with at least two and up to half positively charged phosphorodiamidate linkages. In a preferred embodiment, the uncharged, phosphorus-containing intersubunit linkages are represented by the structure:

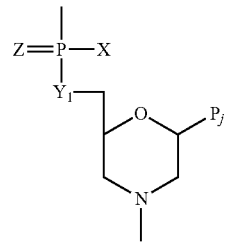

where $Y_1$=O, Z=O, Pj is a purine or pyrimidine base-pairing moiety effective to bind, by base-specific hydrogen bonding, to a base in a polynucleotide (where base-pairing moieties on different subunits may be the same or different), X is alkyl, alkoxy, thioalkoxy, or alkyl amino of the form $NR_2$, where each R is independently hydrogen or methyl, and the positively charged linkages are represented by the same structure, but where X is 1-piperazino.

The compound may be a covalent conjugate of an oligonucleotide analog moiety capable of forming such a heteroduplex structure with the positive or negative sense strand of the virus, and an arginine-rich polypeptide effective to enhance the uptake of the compound into host cells. Exemplary arginine-rich polypeptides have one of the sequences identified by SEQ ID NOS: 41-43.

The oligomer will typically have a $T_m$, with respect to binding to the viral target sequence, of greater than about 50° C., as well as an ability to be actively taken up by mammalian cells. In addition, the compound can generally be recovered, in a heteroduplex form consisting of the oligomer and a complementary portion of the viral genome of the RNA virus, from the serum or urine of a mammalian subject, several hours after being administered to the subject.

In various embodiments, the antiviral compounds are directed against specific viruses or families. For example, selected embodiments include antiviral compounds directed against a picornavirus. Exemplary compounds include those having a targeting sequence having at least 90% homology to a sequence selected from the group consisting of:

(i) SEQ ID NO. 16, for a polio virus of the Mahoney and Sabin strains,
(ii) SEQ ID NO. 17, for a hepatitis A virus,
(iii) SEQ ID NO. 18, for a rhinovirus 14,
(iv) SEQ ID NO. 19, for a rhinovirus 16,
(v) SEQ ID NO. 20, for a rhinovirus 1B,
(vi) SEQ ID NOs. 21 and 22, for an Aphthovirus, and
(vii) SEQ ID NOs 23, 24 and 25, for a coxsackie virus.

Other embodiments include antiviral compounds directed against a calicivirus. Exemplary compounds include those having a targeting sequence having at least 90% homology to a sequence selected from the group consisting of:

(i) SEQ ID NOs. 27, 28, and 29, for a serotype Pan-1 vesivirus,
(ii) SEQ ID NO.30, for a porcine vesivirus,
(iii) SEQ ID NO.31, for a Norwalk virus, and
(iv) SEQ ID NO.32, for a feline vesivirus.

Other embodiments include antiviral compounds directed against a togavirus. For use in inhibition of hepatitis E virus, the compound comprises an oligomer having a targeting sequence having at least 90% homology to a sequence selected from the group consisting of SEQ ID NOs: 33 and 34. Still other embodiments include antiviral compounds directed against a togavirus. For use in inhibition of a hepatitis C flavivirus, the compound comprises an oligomer having a targeting sequence that is complementary to a sequence of at least 12 contiguous bases of the HCV AUG start-site region identified by SEQ ID NO: 37. Exemplary targeting sequences include those having at least 90% homology to SEQ ID NO.35, and 38-40.

In more specific embodiments, the compounds have the exact targeting sequences shown, and/or comprise phosphorodiamidate-linked morpholino oligomers. For example, compounds directed against the serotype Pan-1 vesivirus may comprise a phosphorodiamidate-linked morpholino oligomer (PMO) having a targeting sequence selected from the group consisting of SEQ ID NOs. 27, 28, and 29. A compound directed against the feline vesivirus may comprise a PMO having the targeting sequence SEQ ID NO. 31.

In a related aspect, the invention provides a method of inhibiting replication of an RNA virus from the picornavirus, calicivirus, togavirus or flavivirus families, having a single-stranded, positive sense genome of less than 12 kb, and a first open reading frame that encodes a polyprotein containing multiple functional proteins. The method comprises exposing the virus, or, typically, a cell infected with the virus, to a substantially uncharged morpholino oligomer having (a) a sequence of 12 to 40 subunits, supporting a targeting base sequence that is substantially complementary to a viral target sequence which spans the translation initiation region of the first open reading frame, and (b) a substantially uncharged backbone. In one embodiment of the method, the oligomer is administered to a mammalian subject infected with the virus. Preferred embodiments of the antisense compounds, with respect to properties and structure, are as described above.

In a further aspect, the invention provides a method of confirming the presence of an effective interaction between a picornavirus, calicivirus, togavirus or flavivirus infecting a mammalian subject, and a antisense oligomer targeted against the infecting virus. The method comprises:

(a) administering the oligomer to the subject,
(b) at a selected time after said administration, obtaining a sample of a body fluid from the subject; and
(c) assaying the sample for the presence of a nuclease-resistant heteroduplex comprising the antisense oligomer and a complementary portion of the viral target sequence.

As above, the oligomer has a sequence of 12 to 40 subunits, supporting a targeting base sequence that is substantially complementary to a viral target sequence which spans the translation initiation region of the first open reading frame (ORF1) of the infecting virus. Preferably, the oligomer is a morpholino oligomer, and has phosphorus-containing inter-subunit linkages joining the morpholino nitrogen of one subunit to the 5' exocyclic carbon of an adjacent subunit. As noted above, the linkages are uncharged phosphorodiamidate linkages interspersed with positively charged phosphorodiamidate linkages, the latter constituting at least two and up to half of the total linkages.

This method can be used in determining the effectiveness of treating a picornavirus, calicivirus, togavirus or flavivirus infection by administering the oligomer, by carrying out the described steps of administering, obtaining a sample, and assaying for heteroduplex at periodic intervals throughout a treatment period.

In addition, the method can be used in determining the identity of an infecting picornavirus, calicivirus, togavirus or flavivirus. The family or genus of such a virus can be determined by:

(a) providing a plurality of antisense oligomers, each having a base sequence that is substantially complementary to a viral target sequence of a plurality of known viruses selected from picornaviruses, caliciviruses, togaviruses or flaviviruses, wherein each said viral target sequence is (i) common to a virus family or genus, and (ii) not found in humans;
(b) administering at least one oligomer of the plurality to the subject,
(c) at a selected time after said administering, obtaining a sample of a body fluid from the subject;
(d) assaying the sample for the presence of a nuclease-resistant heteroduplex comprising the antisense oligomer and a complementary portion of the viral target sequence, and
(e) identifying the family or genus of the infecting virus, based on the presence or absence of a heteroduplex comprising an administered antisense oligomer and a complementary portion of said viral target base sequence.

For identification of a specific infecting picornavirus, calicivirus, togavirus or flavivirus, the following further steps can be carried out:

(a) providing a second plurality of antisense oligomers, each having a base sequence that is substantially complementary to a viral target sequence of one of a plurality of known viruses from the family or genus identified in step (e) above, wherein each said viral target sequence is (i) specific to one of said known viruses, and (ii) not found in humans;
(b) administering at least one oligomer of the plurality to the subject,
(c) at a selected time after said administering, obtaining a sample of a body fluid from the subject;
(d) assaying the sample for the presence of a nuclease-resistant heteroduplex comprising the antisense oligomer and a complementary portion of the viral target sequence, and
(e) identifying the infecting virus, based on the presence or absence of a heteroduplex comprising an administered antisense oligomer and a complementary portion of said viral target base sequence.

These and other objects and features of the invention will be more fully appreciated when the following detailed description of the invention is read in conjunction with the accompanying figures

BRIEF DESCRIPTION OF THE DRAWING

FIGS. 4G and 4H show exemplary uncharged and cationic phosphorodiamidate linkages.

DETAILED DESCRIPTION OF THE INVENTION

I. Definitions

Figure 1A:
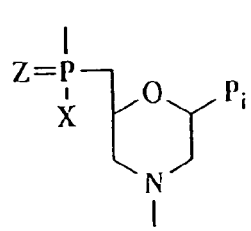
FIGS. 1A-1E show several preferred morpholino-type subunits having 5-atom (A), six-atom (B) and seven-atom (C-E) linking groups suitable for forming polymers.

The terms below, as used herein, have the following meanings, unless indicated otherwise:

The term "open reading frame" or "ORF" refers to a nucleotide sequence that includes a single 5' initiation codon, encodes one or more individual proteins, and terminates at a termination codon.

The terms "polynucleotide", "oligonucleotide", and "oligomer" are used interchangeably and refer to a polymeric molecule having a backbone which supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded RNA, double-stranded RNA, single-stranded DNA or double-stranded DNA). "Polynucleotides" include polymers with nucleotides which are an N- or C-glycoside of a purine or pyriridine base, and polymers containing nonstandard nucleotide backbones, for example, backbones formed using phosphorodiamidate morpholino chemistry, polyamide linkages (e.g., peptide nucleic acids or PNAs) and other synthetic sequence-specific nucleic acid molecules.

A first sequence is an "antisense sequence" with respect to a second sequence if a polynucleotide with a first sequence specifically binds to, or specifically hybridizes with, a polynucleotide which has a second sequence, under physiological conditions.

The terms "antisense oligonucleotide" and "antisense oligomer" refer to a sequence of subunits bearing nucleotide base-pairing moieties, linked by a subunit-to-subunit backbone, that is effective to hybridize to a target sequence of a viral, positive-sense ssRNA. Typically, such an oligomer is from 8 to about 40 nucleotide subunits long, more typically about 12 to 40 nucleotide subunits long, and preferably about 12 to 30, or 12 to 25, subunits in length. The oligomer may have exact sequence complementarity to the target sequence or near complementarity, as defined below. Such an antisense oligomer may block or inhibit the translation of a polyprotein encoded by the target open reading frame (ORF).

A phosphorus containing backbone in an oligonucleotide compound is one in which a majority of the subunit linkages, e.g., between 50-90%, are uncharged at physiological pH, and contain a single phosphorous atom, and at least two and up to half of the linkages have a positive charge at physiological pH. The compound of the invention contains between 8 and 40 subunits, typically about 8-25 subunits, and preferably about 12 to 25 subunits. The compound may have exact sequence complementarity to the target sequence or near complementarity, as defined below.

A "subunit" of an oligonucleotide or oligonucleotide analog refers to one nucleotide (or nucleotide analog) unit of the oligomer. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligomer" is an oligonucleotide analog composed of morpholino subunit structures of the form shown in FIGS. 1A-E, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 1B:
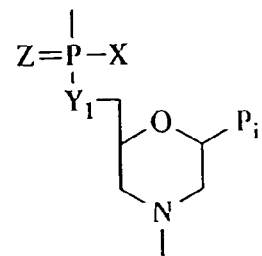
Figure 2A:
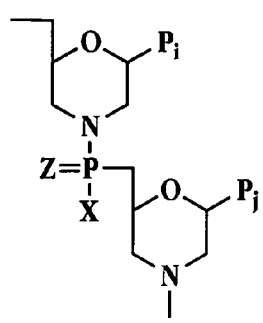
FIGS. 2A-2E show the repeating subunit segment of exemplary morpholino oligonucleotides, designated A through E, constructed using subunits A-E, respectively.
Figure 2B:
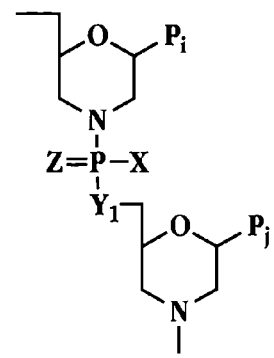

The subunit and linkage shown in FIG. 1B are used for six-atom repeating-unit backbones, as shown in FIG. 2B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

Figure 4A:
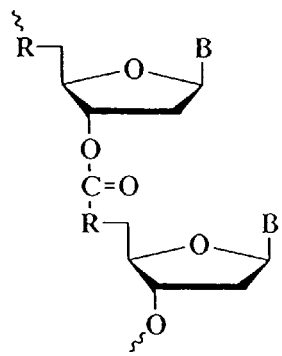
FIGS. 4A-4I show examples of uncharged and charged phosphorodiamidate linkage types in oligonucleotide analogs.
Figure 4B:
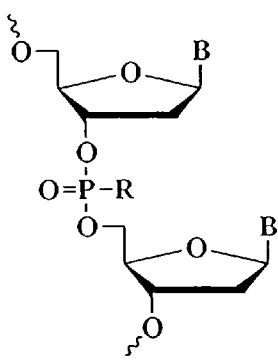
Figure 4C:
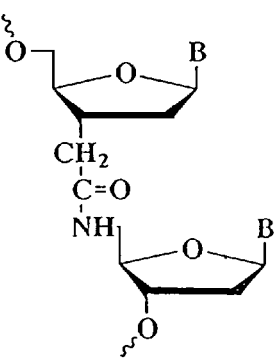
Figure 4D:
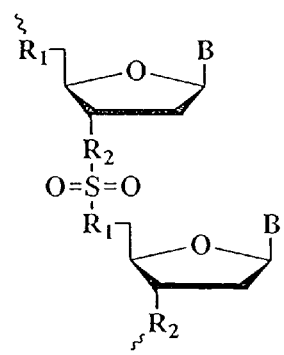
Figure 4E:
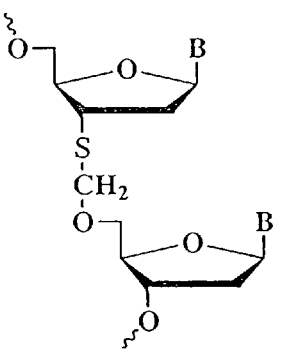
Figure 4F:
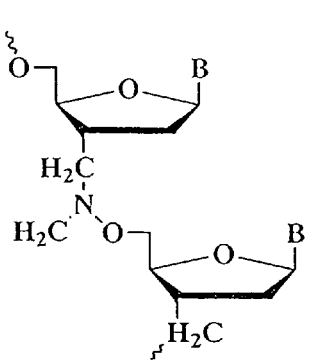
Figure 4G:
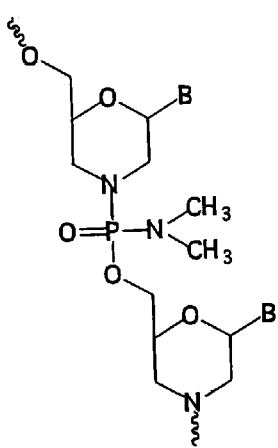
Figure 4H:
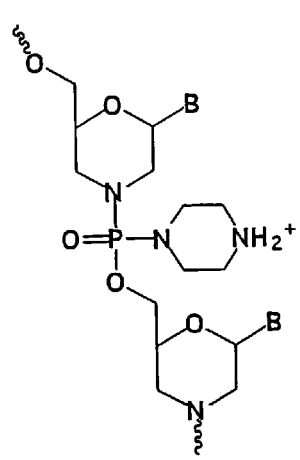
Figure 4I:
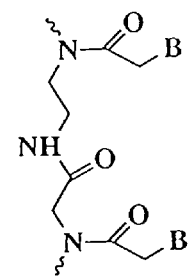

A preferred morpholino oligomer is a phosphorodiamidate-linked morpholino oligomer, referred to herein as a PMO, and includes uncharged phosphorodiamidate linkages interspersed with positively charged phosphorodiamidate linkages. Such oligomers are composed of morpholino subunit structures such as shown in FIG. 1B, where X=NH2, NHR, or NR2 (where R is lower alkyl, preferably methyl), Y=O, and Z=O, and Pi and Pj are purine or pyrimidine base-pairing moieties effective to bind, by base-specific hydrogen bonding, to a base in a polynucleotide, for the uncharged linkages (FIG. 4G), and the same structure, but where X-1-piperazine for the charged linkages (FIG. 4H). The uncharged linkages may also have the structure shown in FIG. 1B, but where X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion (i.e., the percentage) of bases in opposing strands that are expected to form hydrogen bonds with each other, according to generally accepted base-pairing rules. An antisense oligomer may have "near" or "substantial" complementarity to the target sequence and still functional for the purpose of the present invention. Preferably, the antisense oligomers employed have at most one mismatch with the target sequence out of 10 nucleotides, and preferably at most one mismatch out of 20, when compared to the exemplary oligomers having SEQ ID NOs: 16-35 as designated herein. Alternatively, the antisense oligomers employed have at least 90% sequence homology, and preferably at least 95% sequence homology, with the exemplary oligomers having SEQ ID NOs: 16-35 as designated herein.

An oligonucleotide or antisense oligomer "specifically hybridizes" to a target polynucleotide if the oligomer hybridizes to the target under physiological conditions, with a $T_m$ substantially greater than 37° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an antisense oligomer and the complimentary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

As used herein, the term "target", relative to the viral genomic RNA or an mRNA, refers to an mRNA or viral genomic RNA which is expressed or present in single-stranded in one or more types of mammalian cells.

A "base-specific intracellular binding event involving a target RNA" refers to the specific binding of an oligomer to a target RNA sequence inside a cell. The base specificity of such binding is sequence specific. For example, a single-stranded polynucleotide can specifically bind to a single-stranded polynucleotide that is complementary in sequence.

An "antisense oligomer composition" refers to a composition comprising one or more antisense oligomers for use in the RNA detection methods of the present invention. In some cases, such an "antisense oligomer composition" contains a plurality of antisense oligomers.

An "effective amount" of an antisense oligomer, targeted against an infecting ssRNA virus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the antisense agent preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism.

II. Targeted Viruses

The present invention is based on the discovery that effective inhibition of certain classes of small, single-stranded, positive sense RNA viruses can be achieved by exposing cells infected with the virus to antisense compounds (i) targeted against the initiation region of the viral first open reading frame (ORF1) and (ii) having physical and pharmacokinetic features which allow effective interaction between the antisense compound and the virus within host cells. In one aspect, the oligomers can be used in treating a mammalian subject infected with the virus.

The invention targets RNA viruses having genomes that are: (i) single stranded, (ii) positive polarity, (iii) less than 12 kb, and (iv) encoding a polyprotein at the first open reading frame (ORF1). In particular, targeted viral families include picornavirus, calicivirus, togavirus, and flavivirus. Various physical, morphological, and biological characteristics of each of these four families, and members therein, can be found, for example, in *Textbook of Human Virology*, R. Belshe, ed., $2^{nd}$ Edition, Mosby, 1991. Some of the key biological characteristics of each family are summarized below.

A. Picornavirus. The picornaviruses, which infect both humans and animals, can cause severe paralysis (paralytic poliomyelitis), aspectic meningitis, hepatitis, pleurodynia, myocarditis, skin rashes, and colds; inapparent infection is common. Several medically important members include the poliovirus, hepatitis A virus, rhinovirus, Aphthovirus (foot-and mouth disease virus), and the coxsackie virus.

Rhinoviruses are recognized as the cause of the common cold in humans. Serotypes are designated from 1A to 100. Transmission is primarily by the aerosol route and the virus replicates in the nose.

Like all positive sense RNA viruses, the genomic RNA of Picornaviruses is infectious; that is, the genomic RNA is able to direct the synthesis of viral proteins directly, without host transcription events.

B. Calicivirus. The caliciviruses infect both humans and animals. The genus vesivirus produces disease manifestations in mammals that include epithelial blistering and are suspected of being the cause of animal abortion storms and human hepatitis (non A through E) (Smith et al., 1998a and 1998 b). Other genera of the calicivirus include the Norwalk-like and Sapporo-like viruses, which together comprise the human calicivirus, and the lagoviruses, which cause hemorrhagic diseases in rabbits, a particularly rapid and deadly virus.

The human caliciviruses are the most common cause of viral diarrhea outbreaks worldwide in adults, as well as being significant pathogens of infants (O'Ryan et al., 1992). There are at least five types of human caliciviruses that inhabit the gastrointestinal tract. The Norwalk virus is a widespread human agent causing acute epidemic gastroenteritis and causes approximately 10% of all outbreaks of gastroenteritis in man (Murray et al., 1998).

Vesiviruses are now emerging from being regarded as somewhat obscure and host specific to being recognized as one of the more versatile groups of viral pathogens known. For example, a single serotype has been shown to infect a diverse group of 16 different species of animals that include a saltwater fish (opal eye), sea lion, swine, and man.

C. Togavirus. Members of this family include the mosquito-borne viruses which infect both humans and animals. The family includes the genera Alphavirus, Rubivirus (rubella), Pestivirus (mucosal disease), Arterivirus (equine arteritis) and the Hepatitis E virus (HEV).

HEV was initially described in 1987 and first reported in the U.S. in 1991. The virus was initially described as a Calicivirus based on the small, single-stranded RNA character. Some still classify HEV as a Calicivirus, but it has also been classified as a member of the Togavirus family. Infection appears to be much like hepatitis A viral infection. The disease is an acute viral hepatitis which is apparent about 20 days after initial infection, and the virus may be observed for about 20 days in the serum. Transmission occurs through contaminated water and geographically the virus is restricted to less developed countries.

D. Flavivirus. Members of this family include several serious human pathogens, among them mosquito-borne viruses of yellow fever, West Nile fever, hepatitis C, Japanese encephalitis, St. Louis encephalitis, Murray Valley encephalitis, and dengue.

The flavivirus virion is approximately 40 to 50 nm in diameter. The symmetry of the flavivirus nucleocapsid has not been fully defined. It is known that the flavivirus envelope contains only one species of glycoprotein. As yet, no subgenomic messenger RNA nor polyprotein precursors have been detected for the flavivirus.

III. Viral Target Regions

The preferred target sequence is a region that spans the AUG start site of the first open reading frame (ORF1) of the viral genome. The first ORF generally encodes a polyprotein containing non-structural proteins such as polymerases, helicases and proteases. By "spans the AUG start site" is meant that the target sequence includes at least three bases on one side of the AUG start site and at least two bases on the other (a total of at least 8 bases). Preferably, it includes at least four bases on each side of the start site (a total of at least 11 bases).

More generally, preferred target sites include targets that are conserved between a variety of viral isolates. Other favored sites include the IRES (internal ribosome entry site), transactivation protein binding sites, and sites of initiation of replication. Complex and large viral genomes, which may provide multiple redundant genes, may be efficiently targeted by targeting host cellular genes coding for viral entry and host response to viral presence.

A variety of viral-genome sequences are available from well known sources, such as the NCBI Genbank databases. Alternatively, a person skilled in the art can find sequences for many of the subject viruses in the open literature, e.g., by searching for references that disclose sequence information on designated viruses. Once a complete or partial viral sequence is obtained, the ORF1 of the virus is identified. Typically, the ORF1 is identified in the gene database or reference relied on. Alternatively, one may be guided by the general genomic organization of the viruses, as described below for these four families.

The AUG start site of ORF1 may also be identified in the gene database or reference relied upon, or it may be found by scanning the sequence for an AUG codon in the region of the expected ORF1 start site.

The general genomic organization of each of the four virus families is given below, followed by exemplary target sequences obtained for selected members (genera, species or strains) within each family.

A. Picornavirus. FIG. 3A shows the genome structure 10 of a picornavirus, in this case, a rhinovirus of the Picornavirus family. Typical of the picornavirus, the rhinovirus genome 10 is a single molecule of single-stranded, positive sense, polyadenylated RNA of approximately 7.5 kb. As shown, the genome includes a long UTR 12, which is located upstream of the first polyprotein, and a single open reading frame (ORF) having a VPg (viral genome linked) protein covalently attached to its end. The ORF is subdivided into two segments (14, 16), each of which encodes a polyprotein. The first segment 14 encodes a polyprotein that is cleaved subsequently to form viral proteins VP1 to VP4, and the second segment 16 encodes a polyprotein which is the precursor of viral proteins including a Cis-pro, a protease, and a polymerase. The ORF terminates in a polyA termination sequence 18.

The target initial AUG start site is located between base positions 615-640. Targeting this region is effective to inhibit translation of both polyprotein segments 14, 16.

B. Calicivirus. FIG. 3B shows the genome 20 of a calicivirus; in this case, a vesivirus of the Calicivirus family. The genome is a single molecule of infectious, single stranded, positive sense RNA of approximately 7.5 kb. As shown, the genome 20 includes a UTR 22 upstream of the first open reading frame (ORF1) 24 which is unmodified. The 3' end 26 of genome 20 is polyadenylated. Genome 20 includes three open reading frames. The first open reading frame 24 encodes a polyprotein, which is subsequently cleaved to form the viral non-structural proteins including a helicase, a protease, an RNA dependent RNA polymerase, and "VPg", a protein that becomes bound to the 5' end of the viral genomic RNA (Clarke and Lambden, 2000). The second open reading frame 28 codes for the single capsid protein, and the third open reading frame 29 codes for what is reported to be a structural protein that is basic in nature and probably able to associate with RNA (Green et al., 2000).

The target initial AUG start site is located between base positions 7-35. Targeting this region is effective in inhibiting the translation of first reading frame 24.

Figure 3A:
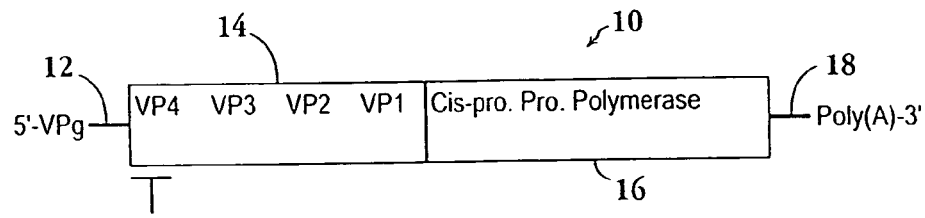
FIGS. 3A-3D are schematic diagrams of genomes of exemplary viruses and viral target sites.
Figure 3B:
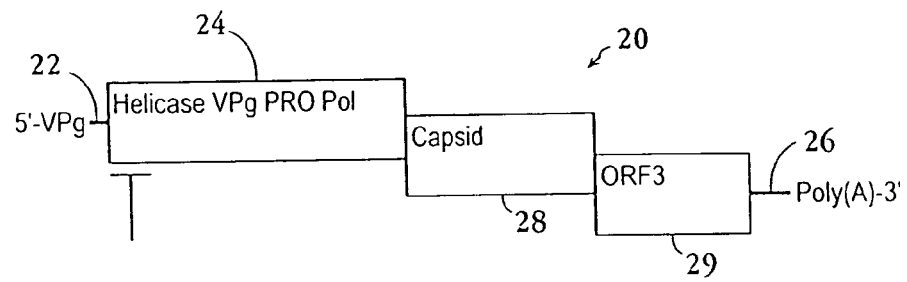
Figure 3C:
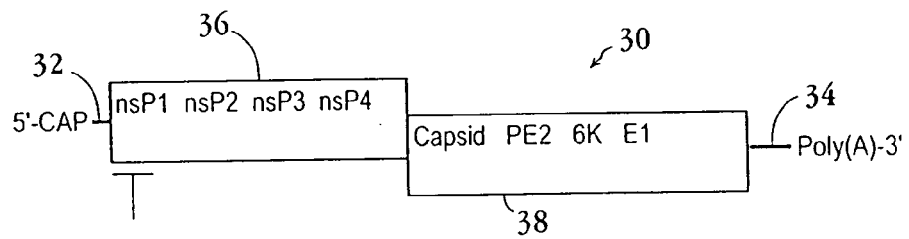

C. Togavirus. FIG. 3C shows the structure of the genome 30 of a togavirus; in this case, a rubella virus of the Togavirus family. Genome 30 is a single linear molecule of single-stranded, positive-sense RNA of approximately 11.7 kb, which is infectious. The 5' end 32 is capped with a 7-methylG molecule and the 3' end 34 is polyadenylated. Full-length and subgenomic messenger RNAs have been demonstrated, and post translational cleavage of polyproteins occurs during RNA replication. Genome 30 includes two open reading frames 36, 38. First open reading frame 36 encodes a polyprotein which is subsequently cleaved into four functional proteins, nsP1 to nsP4. Second open reading frame 38 encodes the viral capsid protein and three other viral proteins, PE2, 6K and E1. The AUG start site for first open reading frame 36 is located between base positions 10-40. Targeting this region is effective to inhibit the translation of first open reading frame 36.

Figure 3D:
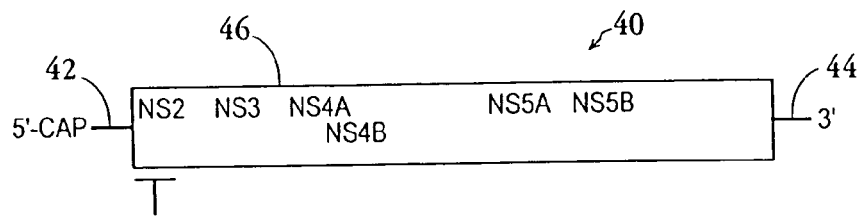

D. Flavivirus. FIG. 3D shows the structure of the genome 40 of the hepatitis C virus of the Flavivirus family. The hepatitis C virus genome is a single linear molecule of single-stranded, positive-sense RNA of about 11 kb. The 5' end 42 is capped with a m$^7$GppAmp molecule, and the 3' end 44 is not polyadenylated. Genome 40 includes only one open reading frame 46 which encodes a precursor polyprotein separable into six structural and functional proteins. The initial AUG start site is located at base position 343.

GenBank references for exemplary viral nucleic acid sequences containing the ORF1 start site in the corresponding viral genomes are listed in Table 3, below. It will be appreciated that these sequences are only illustrative of other sequences in the ORF1 start-site region of members of the four virus families, as may be available from available gene-sequence databases of literature or patent resources. The sequences below, identified as SEQ ID NOs 1-15, are listed in Table 10 at the end of the specification.

TABLE 3

Exemplary Viral Nucleic Acid Sequences Spanning the AUG Site of ORF1

| Virus | GenBank Acc. No. | Nucleotidess (Target Seq.) | SEQ ID NO. |
|---|---|---|---|
| Picornaviridae | | | |
| Poliovirus Mahoney strain | NC 002058 | 735-754 | 1 |
| Poliovirus Sabin strain | V01150 | 735-754 | 2 |
| Hepatitis A | M14707 | 731-754 | 3 |
| Rhinovirus 14 | NC 001490 | 621-640 | 4 |
| Rhinovirus 16 | NC 001752 | 618-637 | 5 |
| Rhinovirus 1B | D00239 | 615-634 | 6 |

TABLE 3-continued

Exemplary Viral Nucleic Acid Sequences Spanning the AUG Site of ORF1

| Virus | GenBank Acc. No. | Nucleotidess (Target Seq.) | SEQ ID NO. |
|---|---|---|---|
| Aphthovirus | NC 003082 | 711-732 | 7 |
| | NC 002554 | 1033-1058 | 8 |
| Coxsackievirus | M16560 | 735-754 | 9 |
| Caliciviridae | | | |
| Vesivirus (Pan-1) | AF091736 | 1-34 | 10 |
| Porcine | AF182760 | 6-25 | 11 |
| Norwalk | AF093797 | 1-19 | 12 |
| Togaviridae | | | |
| Hepatitis E | NC 001434 | 5-28 | 13 |
| | | 1-18 | 14 |
| Flaviviridae | | | |
| Hepatitis C | AF169005 | 330-348 | 15 |
| Hepatitis C | AF169005 | 243-367 | 37 |

As indicated above, the targeting sequence, that is, the base sequence of the antisense oligomer, is preferably directed against an AUG start-site region of the first open reading frame of the virus, typically including up to 100 bases upstream of the start codon, and up to 25 bases downstream thereof. In particular, the targeting sequence is complementary, or substantially complementary, as defined above, to at least 8, and preferably at least 12, typically 12-25 contiguous bases of the AUG start site region of the first open reading frame of the viral genome, and the degree of complementarity between the target and targeting sequence is sufficient to form a stable duplex. In one embodiment, the targeting sequence includes a CAT sequence directed against the AUG codon, and at least three bases on one side of this sequence, and two on the other. In other embodiments, the targeting sequence is complementary to a sequence in the start-site region that is entirely upstream or entirely downstream of the AUG start site. An antisense oligomer of about 15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., *Nucleic Acid Hybridization*, IRL Press, 1985, pp. 107-108. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 15 bases or less are generally preferred over those requiring 20+ bases for high $T_m$ values.

Figure 2C:
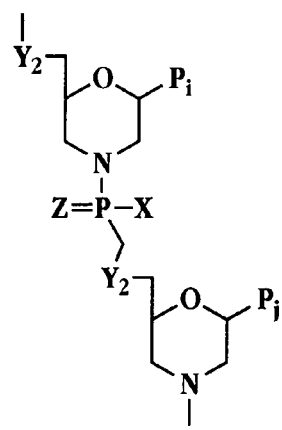
Figure 2D:
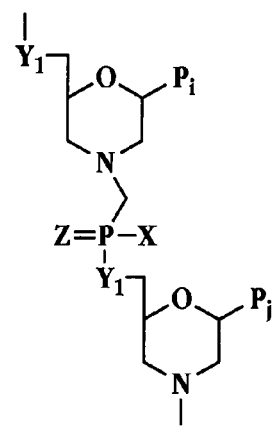
Figure 2E:
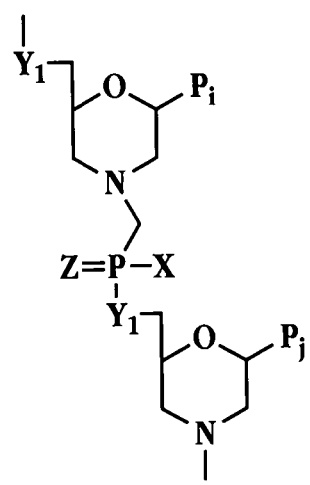

According to one aspect of the invention, the antisense activity of the oligomer is enhanced by using a mixture of uncharged and cationic phosphorodiamidate linkages as shown in FIGS. 2E and 2F. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Table 4 lists exemplary targeting sequences directed against a target region that spans the translation initiation site of the first open reading frame (ORF1) of selected viruses of the picornavirus, calicivirus, togavirus, and flavivirus families. These sequences were selected, as indicated above, by constructing a complementary sequence to one or more sequences spanning the AUG site in the target sequences given above.

Exceptions to this general rule are the following: SEQ ID NO: 26 is directed to the origin of the viral genome; SEQ ID NOs: 23-25 contain mismatches and/or inserts, as indicated by underlining; and SEQ ID NO: 33 includes only one base of the ATG start codon.

TABLE 4

Exemplary Antisense Sequences Targeting the ORF1 Translation Initiation Region

| Virus | GenBank Acc. No. | Targeted Region | Antisense Oligomer (5' to 3) | Seq. ID No. |
|---|---|---|---|---|
| Picornaviridae Poliovirus | | | | |
| Mahoney strain | NC002058 | 735-755 | CCTGAGCACCCATTATGATAC | 16 |
| Sabin strain | V01150 | 735-755 | | |
| Hepatitis A | M14707 | 731-754 | CCTTGTCTAGACATGTTCATTATT | 17 |
| Rhinovirus 14 | NC001490 | 621-640 | CTGAGCGCCCATGATCACAG | 18 |
| Rhinovirus 16 | NC001752 | 618-637 | TTGAGCGCCCATGATAACAA | 19 |
| Rhinovirus 1B | D00239 | 615-634 | CTGGGCACCCATGATGCCAA | 20 |
| Aphthovirus | NC003082 | 711-732 | AAACAGTCAGTTGTGCTCATTG | 21 |
| | NC002554 | 1037-1058 | AAACAGTCAGTTGTATTCATAG | 22 |
| Coxsackievirus | M16560 | 735-754 | CTTGAGCTCCCATTTTGCTG | 23 |
| | | | CTTGAGCCCCCATTTTTGTTG | 24 |
| | | | CCTGTGCTCCCATCTTGATG | 25 |
| | | 1-30 | TGGGTGGGATCAACCCACAGGCTGTTT TAA | 26 |
| Caliciviridae | | | | |
| Vesivirus (Pan-1) | AF091736 | 7-26 | GAGCCATAGCTCAAATTCTC | 27 |
| | | 1-21 | TAGCTCAAATTCTCATTTAC | 28 |
| | | 15-34 | GAGCGTTTGAGCCATAGCTC | 29 |
| Porcine | AF182760 | 6-25 | GACGGCAATTAGCCATCACG | 30 |
| Norwalk | AF093797 | 1-19 | CGACGCCATCATCATTCAC | 31 |
| Feline | AF479590 | 14-34 | CAGAGTTTGAGACATTGTCTC | 32 |
| Togaviridae | | | | |
| Hepatitis E | NC001434 | 6-28 | CCTTAATAAACTGATGGGCCTCC | 33 |
| | | 1-18 | CTGATGGGCCTCCATGGC | 34 |

TABLE 4-continued

Exemplary Antisense Sequences Targeting the ORF1 Translation Initiation Region

| Virus | GenBank Acc. No. | Targeted Region | Antisense Oligomer (5' to 3) | Seq. ID No. |
|---|---|---|---|---|
| Flaviviridae | | | | |
| Hepatitis C | AF169005 | 348-330 | GTGCTCATGGTGCACGGTC-3 | 35 |
| | | | GGCCTTTCGCGACCCAACAC | 38 |
| | | | ATCAGGCAGTACCACAAGGC | 39 |
| | | | CACGGTCTACGAGACCTCCC | 40 |

IV. Antisense Oligomers

A. Properties

As detailed above, the oligomer has a base sequence directed against a targeted portion of the viral genome, preferably spanning the ORF1 start site. In addition, the oligomer is able to effectively target infecting viruses, when administered to an infected host cell, e.g. in an infected mammalian subject.

The latter requirement is met when the oligomer compound (a) has the ability to be actively taken up by mammalian cells, and (b) once taken up, form a duplex with the target ssRNA with a $T_m$ of greater than about 50° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense with respect to the target, the ratio of G:C to A:T base matches, and the positions of any mismatched bases. The ability of the antisense agent to resist cellular nucleases promotes survival and ultimate delivery of the agent to the cell cytoplasm.

Below are disclosed methods for testing any given, substantially uncharged backbone for its ability to meet these requirements.

A1. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, 2000). The net charge is preferably neutral or at most 1-2 net charges per oligomer.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenylalanine and cysteine. The peptide may also contain non-natural amino acids such as beta-alanine and 6-aminohexanoic acid. Exemplary arginine-rich peptide are listed as SEQ ID NOS: 41-43. The use of arginine-rich peptide-PMO conjugates can be used to enhance cellular uptake of the antisense oligomer (See, e.g. (Moulton, Nelson et al. 2004). Single letter codes for amino acids are used expect for the non-natural amino acids beta-alanine (β-Ala) and 6-aminohexanoic acid (Ahx).

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

The antisense compound may be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner et al., 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

A2. Substantial Resistance to RNaseH

Two general mechanisms have been proposed to account for inhibition of expression by antisense oligonucleotides. (See e.g., Agrawal et al., 1990; Bonham et al., 1995; and Boudvillain et al., 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). However, because such compounds would expose the viral RNA in an oligomer:RNA duplex structure to proteolysis by RNaseH, and therefore loss of duplex, they are suboptimal for use in the present invention.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme et al., 1996), morpholino oligonucleotides, peptide nucleic acids (PNA's), certain 2'-O-allyl or 2'-O-alkyl modified oligonucleotides (Bonham, 1995), and N3'→P5' phosphoramidates (Gee, 1998; Ding, 1996).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

A3. In vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. Patent applications, Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as the translation initiation region of ORF1, as described above), the method can be used to detect the presence of a given ssRNA virus, or reduction in the amount of virus during a treatment method.

B. Exemplary Oligomer Backbones

Examples of nonionic linkages that may be used in oligonucleotide analogs are shown in FIGS. 4A-4H. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (4A, R=O) and carbamate (4A, R=NH$_2$) linkages, (Mertes, 1969; Gait, 1974); alkyl phosphonate and phosphotriester linkages (4B, R=alkyl or —O-alkyl) (Miller, 1993; Lesnikowski, 1990); amide linkages (4C) (Bloomers, 1994); sulfone and sulfonamide linkages (4D, R$_1$, R$_2$=CH$_2$) (Roughten, 1995; McElroy, 1994); and a thioformacetyl linkage (4E) (Matteucci, 1990; Cross, 1997). The latter is reported to have enhanced duplex and triplex stability with respect to phosphorothioate antisense compounds (Cross, 1997). Also reported are the 3'-methylene-N-methylhydroxyamino compounds of structure 4F (Mohan, 1995).

Peptide nucleic acids (PNAs) (FIG. 4G) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages interspersed with cationic linkages, as described above. Especially preferred is a substantially uncharged and cationic phosphorodiamidate-linked morpholino oligomer, such as illustrated in FIG. 4H and in FIG. 2B-B. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits shown in FIGS. 1A-E include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer: RNA heteroduplex to resist RNAse degradation.

Figure 1C:
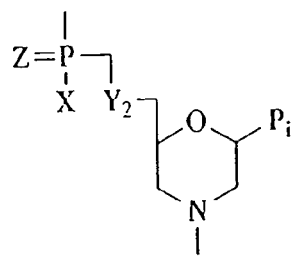
Figure 1D:
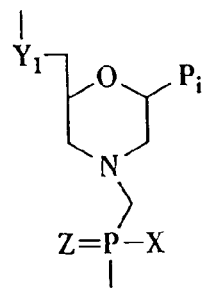
Figure 1E:
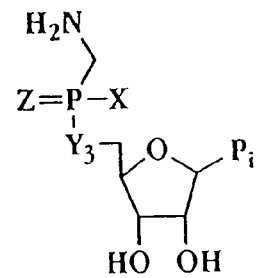

Exemplary backbone structures for antisense oligonucleotides of the invention include the β-morpholino subunit types shown in FIGS. 1A-E, each linked by an uncharged, phosphorus-containing subunit linkage. FIG. 1A shows a phosphorus-containing linkage which forms the five atom repeating-unit backbone shown FIG. 2A, where the morpholino rings are linked by a 1-atom phosphoamide linkage. FIG. 1B shows a linkage which produces a 6-atom repeating-unit backbone, as shown in FIG. 2B. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen. The linkage shown in FIGS. 1C-E are designed for 7-atom unit-length backbones, as shown for structures in FIGS. 2C-E. In Structure 2C, the X moiety is as in Structure 2B, and the moiety Y may be methylene, sulfur, or, preferably, oxygen. In Structure 2D, the X and Y moieties are as in Structure 2B. In structure 2E, X is as in Structure 2B, and Y is O, S, or NR, where R is hydrogen or lower alkyl, preferably hydrogen or methyl. In all subunits depicted in FIGS. 2A-E, Z is O or S, and each of $P_i$ and $P_j$ is a base pairing moiety, preferably selected from adenine, cytosine, guanine and uracil.

Particularly preferred morpholino oligonucleotides include those composed of morpholino subunit structures of the form shown in FIG. 2B, where X=$NH_2$ or $N(CH_3)_2$, Y=O, and Z=O. As noted above, the morpholino compound of the invention includes a limited number of positively charged backbone linkages. One example of a cationic charged phophordiamidate linkage is shown in FIG. 2F. This linkage, in which the dimethylamino group shown in FIG. 2E is replaced by a 1-piperazino group as shown in FIG. 2F, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by a subject without undesirable side effects. The method for synthesizing the 1-piperazino group linkages is described below with respect to FIG. 7.

V. Inhibition of Viral Replication

The antisense compounds detailed above are useful in inhibiting replication of ssRNA viruses of the picornavirus, calicivirus, togavirus, and flavivirus families. In one embodiment, such inhibition is effective in treating infection of a host animal by these viruses. Accordingly, the method comprises, in one embodiment, contacting a cell infected with the virus with an antisense agent effective to inhibit the translation of a polyprotein encoded in the first open reading frame of the genome of the specific virus. In a further embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific virus causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting broad families and/or genera of viruses, e.g., Picornaviridae, Caliciviridae, Togaviridae and Flaviviridae. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of an antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., *Leukemia* 10(12):1980-1989, 1996; Lappalainen et al., *Antiviral Res.* 23:119, 1994; Uhlmann et al., ANTISENSE OLIGONUCLEOTIDES: A NEW THERAPEUTIC PRINCIPLE, *Chemical Reviews*, Volume 90, No. 4, pages 544-584, 1990; Gregoriadis, G., Chapter 14, Liposomes, *Drug Carriers in Biology and Medicine*, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., *J. Biol. Chem.* 262:4429-4432, 1987)

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (IV).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-25 mg oligomer per 70 kg. In some cases, doses of greater than 25 mg oligomer/patient may be necessary. For IV administration, preferred doses are from about 0.5 mg to 10 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., *Antimicrob. Agents and Chemotherapy* 39(5):1157-1161, 1995; Anderson, K. P. et al., *Antimicrob. Agents and Chemotherapy* 40(9):2004-2011, 1996, Cottral, G. E. (ed) in: Manual of Standard Methods for Veterinary Microbiology, pp. 60-93, 1978).

A preferred method of monitoring the efficacy of the antisense treatment is by detection of the antisense-RNA heteroduplex. At selected time(s) after antisense administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml of less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

EXAMPLES

The following examples illustrate but are not intended in any way to limit the invention.

Materials and Methods

Standard recombinant DNA techniques were employed in all constructions, as described in Ausubel, F M et al., in CURRENT PROTOCOLS IN MOLECULAR BIOLOGY, John Wiley and Sons, Inc., Media, Pa., 1992 and Sambrook, J. et al., in MOLECULAR CLONING: A LABORATORY MANUAL, Cold Spring Harbor Laboratory Press, Cold Spring Harbor, N.Y., Vol. 2, 1989).

Example 1

Antisense Inhibition of Picornaviridae (Human rhinovirus) in vitro

The inhibitory effect on rhinovirus 16 of a phosphorodiamidate morpholino oligomer (PMO) having a sequence targeted to the translation initiation zone of rhinovirus 14 was evaluated. The phosphorodiamidate morpholino oligomers (PMO) were synthesized at AVI BioPharma (Corvallis, Oreg.), as described in Summerton and Weller, 1997. Purity of the full-length oligomer was greater than 90% as determined by reverse-phase high-pressure liquid chromatography and MALDI TOF mass spectroscopy. The lyophilized PMOs were dissolved in sterile 0.9% NaCl and filtered through 0.2 µm Acrodisc filters (Gelman Sciences, Ann Arbor, Mich.) prior to use in cell cultures.

The PMO includes a nucleic acid sequence targeting rhinovirus 14 and containing three mispairs in respect to the rhinovirus 16 target sequence. The target sequence (GenBank NC001752 618-637; SEQ ID NO: 5) and targeting sequence (SEQ ID NO: 18) are as follows:

```
HRV-16:
TTGTTATCATGGGCGCTCAA         SEQ ID NO: 5

HRV-14 antisense:
GACACTAGTACCCGCGAGTC         SEQ ID NO: 18
``` where the bolded codon is the start codon, and the mispairs are underlined.

Figure 7:
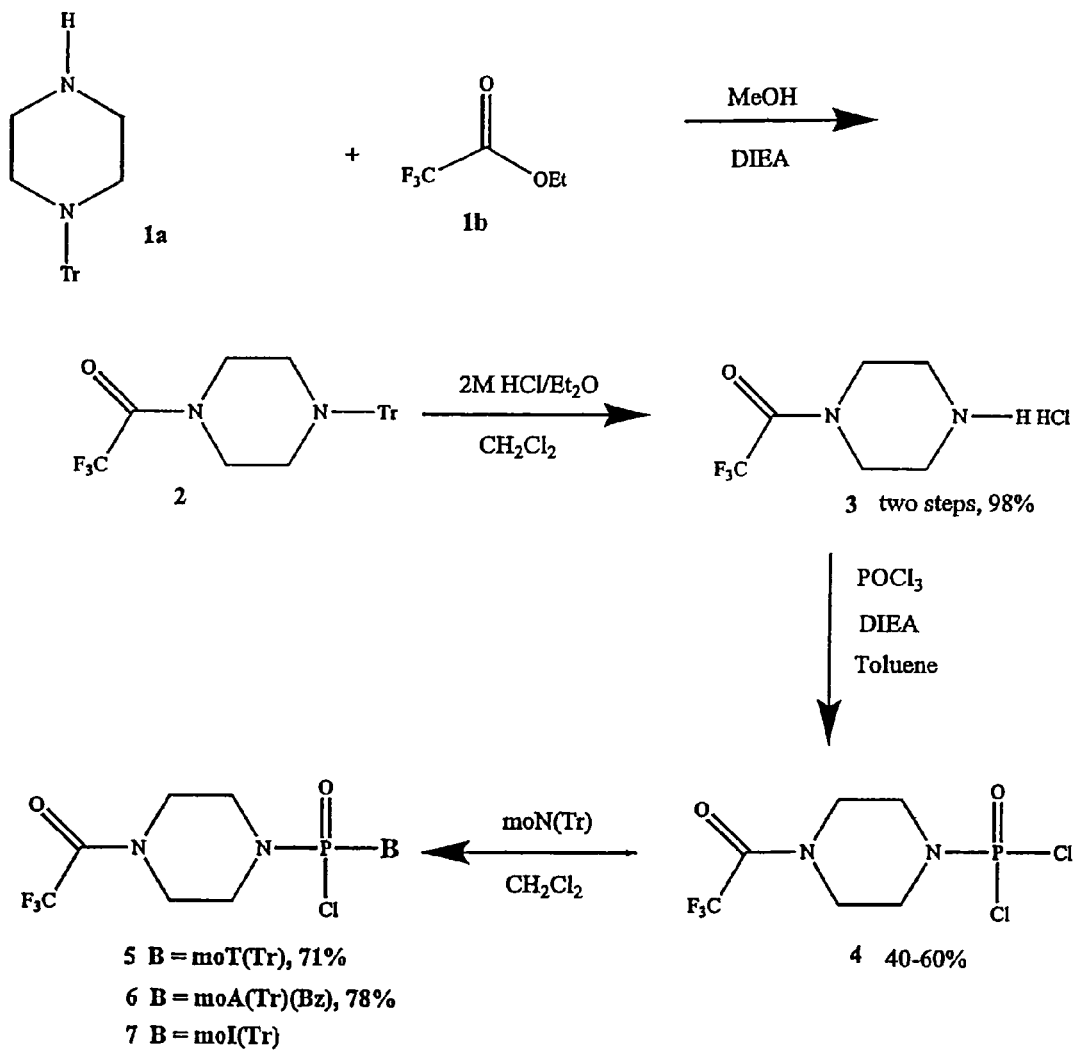
FIG. 7 shows the synthetic steps to produce subunits used to produce +PMO containing the (1-piperazino) phosphinylideneoxy cationic linkage as shown in FIG. 4H.

A schematic of a synthetic pathway that can be used to make morpholino subunits containing a (1 piperazino) phosphinylideneoxy linkage is shown in FIG. 7; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5, 6, 7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

Twenty-four hour old cultures of HeLa cells were grown in six well plates for 24 hours. Confluent monolayers were propagated in Earles minimal essential medium (MEM) supplemented with 5% bovine calf serum, L-glutamine, antibiotics, and sodium bicarbonate. Cells were incubated at 37° C. in a 5% $CO_2$ humidified atmosphere. Prior to treatment, the monolayers were rinsed twice with MEM without serum.

Figure 5:
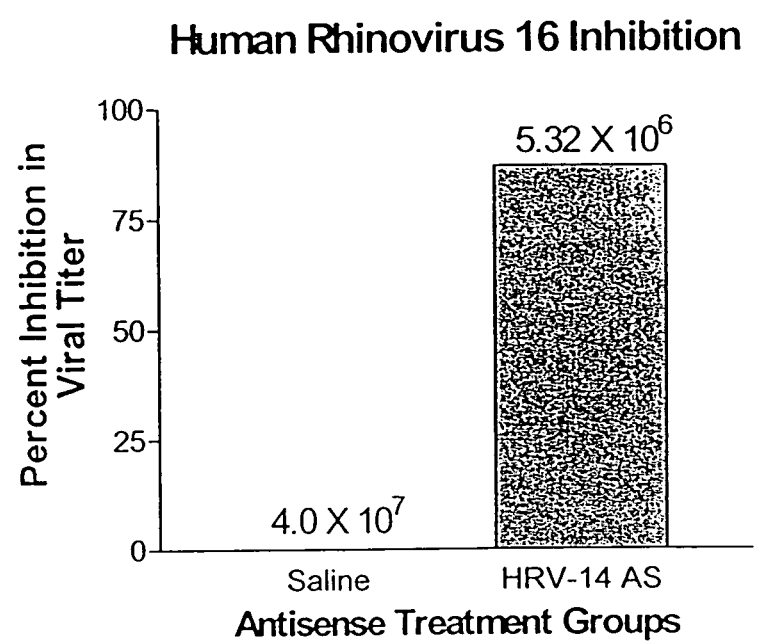
FIG. 5 shows percent inhibition of human rhinovirus in vitro in the presence of an antisense oligomer of the invention, having three base mismatches with the viral sequence, as described in Example 1.

The PMOs were introduced into the cultured cells by a "scrape-loading" method, which is known to deliver PMOs to 80-90% of the adherent cells in the culture (Partridge et al., 1996). The oligomers were diluted to a final concentration of 20 µM in MEM without serum. A 0.5 ml volume of oligomer-MEM media was added to the cultures and after 1 minute at room temperature the cells were gently scraped off with a rubber policeman. The cells were returned to the $CO_2$ incubator for 10 minutes, then diluted into 8 ml of MEM with calf serum and dispersed in 0.1 ml per well of a 96-well plate containing log dilutions of rhinovirus 16 (8 wells per dilution). The plates were incubated for 72 hours at 37° C. in the $CO_2$ incubator, after which time they were examined with an Olympus CK light microscope for the presence of cytopathic effect. Viral titers (TCID50) were determined by the method of Spearman-Karber. Viral titer for the different treatment groups is shown in Table 6 below and graphically in FIG. 5.

TABLE 6

| Treatment | Viral Titer |
| --- | --- |
| saline | $4.0 \times 10^7$ |
| HRV-14 AS | $5.32 \times 10^6$ |

The results show greater than 75% inhibition of the viral titer of HRV-16 when treated with PMO antisense to the HRV-14. While efficacy is lower than the efficacy of rhinovirus 16 targeting sequence directed against rhinovirus 16 infection, demonstrated in a previous study, as expected from the three mismatched basepairs, the study confirms the antiviral effects of PMOs substantially complementary to the translation initiation zone of the HRV-16 genome.

Example 2

Antisense Inhibition of Caliciviridae Vesivirus Isolates PCV Pan-1 and SMSV-13 in Porcine Kidney (PK-15) and African Green Monkey Kidney (Vero) Tissue Culture The antiviral efficacy of three phosphorodiamidate morpholino oligomers (PMO) targeted to the ORF1 translation initiation zone of the strains Pan-1 and SMSV-13 of the vesivirus genus of *Caliciviridae* was evaluated. The PMOs were scrape-loaded, as described above, to two host cell lines, Porcine kidney cells (PK-15) (ATCC No. CCL33) and African Green Monkey Kidney cells (ATCC No. CCL81) (Vero), which were subsequently exposed to vesiviruses of the strains Pan-1 and SMSV-13. The protocol of Example 1 was followed for incubation and determination of viral load.

The three PMOs each included a targeting sequence complementary to the Pan-1 sequence (GenBank accession no. AF091736) spanning the start codon of ORF1. PMOs were used at a concentration of 20 μm in serum free media. A saline blank and scrambled sequence control PMO were included in the study. The PMO sequences, identified as ORF1.1 (SEQ ID NO. 27), ORF1.2 (SEQ ID NO. 28), and ORF1.3 (SEQ ID NO. 29), and the target site locations are listed in Table 7 below.

TABLE 7

Oligomer Sequences and Target Locations

| Oligomer | Target Location in Pan-1 | Sequence, 3' | SEQ ID NO: |
|---|---|---|---|
| ORF1.1 | 7-26 | GAG CCA TAG CTC AAA TTC TC | 27 |
| ORF1.2 | 1-21 | TAG CTC AAA TTC TCA TTT AC | 28 |
| ORF1.3 | 15-34 | GAG CGT TTG AGC CAT AGC TC | 29 |
| Scrambled control | — | GAC ATA TCT AAT CAT ATA C | 36 |

The inhibitory effects of the PMOs on the viral titer of SMSV-13 and Pan-1 in both PK-15 and Vero cells are provided in Table 8. A simple percent inhibition average is presented when both cell types were tested with a given viral strain.

TABLE 8

Effects of antisense PMOs on viral titers of vesiviruses, strains PCV Pan-1 and SMSV-13, in PK-15 and Vero host cells.

| PMO (20 μM) | VMK cells ($TCID_{50}$/ml) | PK-15 cells ($TCID_{50}$/ml) | % Inhib. (Avg) |
|---|---|---|---|
| | Virus strain SMSV-13 | | |
| Saline | $5.3 \times 10^7$ | $7.1 \times 10^5$ | 0 |
| ORF1.1 | $1.7 \times 10^7$ | $5.3 \times 10^4$ | 80 |
| ORF1.2 | $3.0 \times 10^7$ | | 43 |
| ORF1.3 | $1.7 \times 10^7$ | $3.0 \times 10^5$ | 68 |
| Scrambled control | $7.1 \times 10^7$ | $9.5 \times 10^5$ | −33 |
| | Virus strain Pan-1 | | |
| Saline | $7.1 \times 10^6$ | $2.2 \times 10^6$ | 0 |
| ORF1.1 | $1.3 \times 10^6$ | $3.0 \times 10^5$ | 84 |
| ORF1.2 | $2.2 \times 10^6$ | | 68 |
| ORF1.3 | $4.0 \times 10^6$ | | 44 |
| Scrambled control | | $2.3 \times 10^6$ | −5 |

Significant inhibition of viral titer was observed with the ORF1-targeting PMOs in both cell lines and for both viral serotypes, with "ORF1.1" being most effective. The scrambled control PMO had no inhibitory effect.

In dose response studies, Vero cells were loaded with PMOs having ORF1.1 and ORF1.3 targeting sequences and subsequently exposed to vesivirus strain SMSV-13, following the protocol described in Example 1. Treatment with the ORF1.1 PMO gave no inhibition at 0.2 and 1.0 μM, moderation inhibition at 2.0 μM, and high inhibition at 20 μM. The ORF1.3 PMO gave no inhibition of SMSV-13 viral titer at 0.2 μM, but inhibition was high at 1.0 μM; no additional inhibition was observed at 2, 10, and 20 μM.

Example 3

Effect of PMO Antisense to Feline Calicivirus

A feline calicivirus that became a hemorrhagic virus to the cat was isolated and propagated in a cell culture. The cell culture was exposed, following the protocol described in Example 1, to an antisense PMO having the following targeting sequence: CAG AGT TTG AGA CAT TGT CTC (SEQ ID No. 32). A one-log reduction of viral titer was observed in the cell culture.

Example 4

Effect of an Antisense PMO Targeted to HCV Viremia in HCV-Trimera Mice

The study was performed on pathogen-free female CB6F1 and SCID/beige mice obtained from Harlan Inc. (reared and maintained in the Weizmann Institute Animal Breeding Center). The mice were housed in a specific pathogen-free environment; allowed sterile food and acidified water ad lib prior to initiation of the study.

CB6F1 mice were thymectomized at the age of 7-9 weeks. Experiments were performed using CB6F1 mice at the age of 12-18 weeks (19-25 g/mouse). Prior to heterotransplantation, the CB6F1 mice received a split dose of total body irradiation (4 Gy followed 1 day later by 11 Gy) from a gamma beam 150-A $^{60}$Co source (Atomic Energy of Canada) with irradiation rate of 0.7 Gy/min. After the first irradiation, ciprofloxacin (20 μg/ml; Bayer) was added to drinking water for 7-10 days. Immediately after the second radiation dose, mice were injected i.v. with 4-6×10$^6$ bone-marrow cells (in 0.2 ml PBS) obtained from 6-10 weeks old SCID/beige mice.

CB6F1 mice were anesthetized with 10 mg/mouse of 2,2,2 tribromoethanol (Aldrich) and a laparotomy performed. Human liver fragments infected ex vivo with hepatitis C virus (HCV) were transplanted behind the ear pinna. The incisions were closed with 9 mm autoclip wound clips.

The mice were treated with PMO antisense to the HCV nucleic sequence spanning the AUG site of the first open reading frame, having the targeting sequence GTG CTC ATG GTG CAG GGT C (SEQ ID No. 35). Treatments with the antisense compound or with saline were given from day 10 to day 17 post transplantation (total of 7 days) to four mice groups, containing approximately 17 animals each. PMO doses of 0.01, 0.03 and 0.1 mg/mouse/day were used. Bleeds were taken at days 16 (one day post treatment completion) and 21, and serum samples were evaluated.

Figure 6:
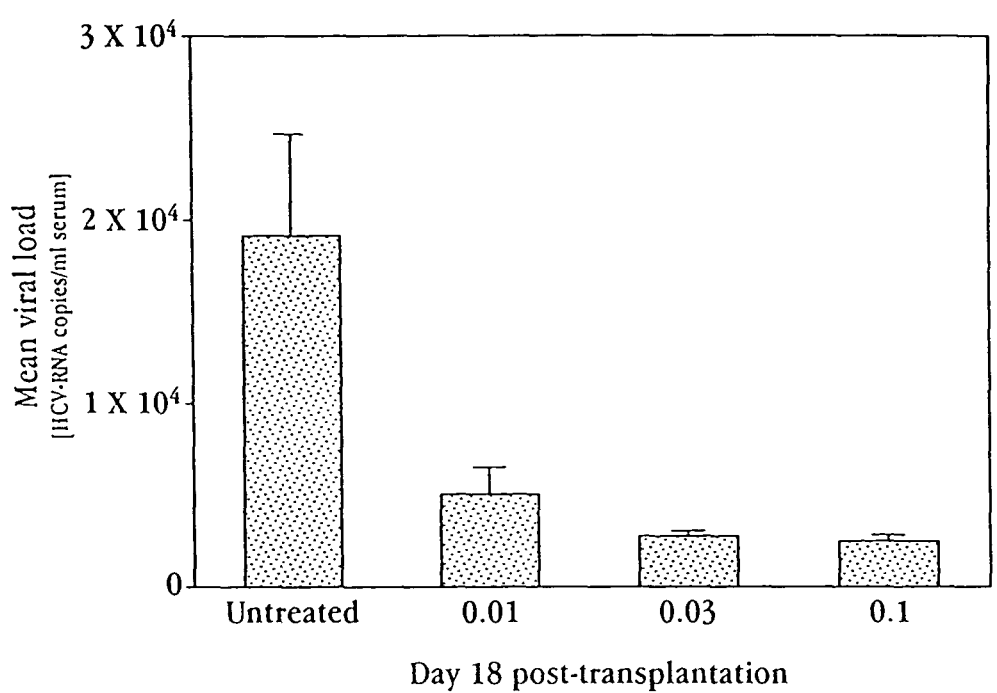
FIG. 6 shows dose response data for an antisense oligomer of the invention in treating HCV infection in mice, as described in Example 4; doses are given in mg/mouse/day.

Results are summarized in Table 9 and shown graphically in FIG. 6. Viral loads are given as Mean Viral Load±SD (HCV-RNA copies/ml serum). Differences in percentages of HCV-positive animals between control and treated groups of mice are compared using the $\chi^2$ analysis. Differences in viral loads between control and treated groups of mice (group pairs) are compared by the non-parametric Mann-Whitney U test.

TABLE 9

In vivo Antisense Dose-Response Efficacy Studies

| Group | Viral Load | Percent HCV positive animals | P value |
|---|---|---|---|
| Saline | $1.91 \times 10^4 \pm 5.58 \times 10^3$ | 65 | n = 17 |
| 0.01 mg/day | $5.00 \times 10^3 \pm 1.39 \times 10^3$ | 29 | 0.03, n = 17 |
| 0.03 mg/day | $2.79 \times 10^3 \pm 2.01 \times 10^2$ | 12 | 0.004, n = 17 |
| 0.10 mg/day | $2.64 \times 10^3 \pm 1.39 \times 10^2$ | 6 | 0.002, n = 18 |

From the foregoing, it will be appreciated that specific embodiments of the invention have been described herein for purposes of illustration, but that various modifications may be made without deviating from the spirit and scope of the invention. Accordingly, the invention is not limited except as by the appended claims.

TABLE 10

Sequence Listing Table

| SEQ ID NO. | Sequence, 5' to 3' |
|---|---|
| 1 | GTATCATAATGGGTGCTCAG |
| 2 | GTATCATAATGGGTGCTCAG |
| 3 | AATAATGAACATGTCTAGACAAGG |
| 4 | CTGTGATCATGGGCGCTCAG |
| 5 | TTGTTATCATGGGCGCTCAA |
| 6 | TTGGCATCATGGGTGCCCAG |
| 7 | CAATGAGCACAACTGACTGTTT |
| 8 | GACCCTATGAATACAACTGACTGTTT |
| 9 | CAACAAAATGGGGGCTCAAG |
| 10 | GTAAATGAGAATTTGAGCTATGGCTCAAACGCTC |
| 11 | CGTGATGGCTAATTGCCGTC |
| 12 | GTGAATGATGATGGCGTCG |
| 13 | TGGAGGCCCATCAGTTTATTAAGG |
| 14 | GCCATGGAGGCCCATCAG |
| 15 | GACCGTGCACCATGAGCAC |
| 16 | CCTGAGCACCCATTATGATAC |
| 17 | CCTTGTCTAGACATGTTCATTATT |
| 18 | CTGAGCGCCCATGATCACAG |
| 19 | TTGAGCGCCCATGATAACAA |
| 20 | CTGGGCACCCATGATGCCAA |
| 21 | AAACAGTCAGTTGTGCTCATTG |
| 22 | AAACAGTCAGTTGTATTCATAG |
| 23 | CTTGAGCTCCCATTTTGCTG |
| 24 | CTTGAGCCCCCATTTTTGTTG |
| 25 | CCTGTGCTCCCATCTTGATG |
| 26 | TGGGTGGGATCAACCCACAGGCTGTTTTAA |
| 27 | GAGCCATAGCTCAAATTCTC |
| 28 | TAGCTCAAATTCTCATTTAC |
| 29 | GAGCGTTTGAGCCATAGCTC |
| 30 | GACGGCAATTAGCCATCACG |
| 31 | CGACGCCATCATCATTCAC |
| 32 | CAGAGTTTGAGACATTGTCTC |
| 33 | CCTTAATAAACTGATGGGCCTCC |
| 34 | CTGATGGGCCTCCATGGC |
| 35 | GTGCTCATGGTGCACGGTC |
| 36 | GACATATCTAATCATATAC |
| 37 | AAGACTGCTAGCCGAGTAGTGTTGGGTCGCGAAAGGCCTTGTGGTAC TGCCTGATAGGGTGCTTGCGAGTGCCCCGGGAGGTCTCGTAGACCGT GCACCATGAGCACGAATCCTAAACCTCAAAG |
| 38 | GGCCTTTCGCGACCCAACAC |
| 39 | ATCAGGCAGTACCACAAGGC |
| 40 | CACGGTCTACGAGACCTCCC |
| 41 | NH$_2$-RRRRRRRRRFFAhxβAla-COOH |
| 42 | NH$_2$-(RAhxR)$_4$AhxβAla-COOH |
| 43 | NH$_2$-(Rkhx)$_8$βAla-COOH |

It is claimed:

1. A method of inhibiting infection by an HCV virus in a subject, comprising administering to the subject, a therapeutically effective amount of a morpholino oligonucleotide composed of 12 to 30 morpholino subunits that is substantially complementary to the target sequence set forth in SEQ ID NO:37, wherein the oligonucleotide has a $T_m$, with respect to binding to the target sequence of greater than about 50° C., and wherein the morpholino subunits are linked by uncharged phosphorodiamidate linkages interspersed with at least two and up to eight phosphorodiamidate linkages containing piperazine groups.

2. The method of claim 1, wherein said morpholino subunits are joined by phosphorodiamidate linkages, in accordance with the structure:

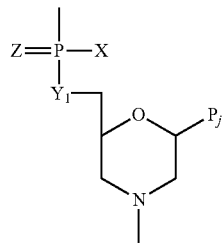

where $Y_1$=O, Z=O, Pj is a purine or pyrimidine base-pairing moiety effective to bind, by base-specific hydrogen bonding, to a base in a polynucleotide (where base-pairing moieties on different subunits may be the same or different), and X is alkyl, alkoxy, thioalkoxy, or alkyl amino of the form $NR_2$, where each R is independently hydrogen or methyl, for the uncharged linkages, and the phosphorodiamidate linkages containing piperazine groups are represented by the same structure, but where X is 1-piperazino.

3. The method of claim 1, wherein the oligonucleotide is actively taken up by mammalian cells.

4. The method of claim 1, wherein the oligonucleotide is complementary to at least 8 contiguous bases of SEQ ID NO:15.

5. The method of claim 1, wherein an arginine-rich peptide is linked covalently to the 5' or 3' end of the oligonucleotide.

6. The method of claim 5, wherein the arginine-rich peptide is about 8-16 amino acids.

7. The method of claim 5, wherein the arginine-rich peptide is selected from SEQ ID NOS:41-43.

8. The method of claim 1, wherein the oligonucleotide is composed of 12 to 25 morpholino subunits.

9. The method of claim 8, wherein the oligonucleotide is complementary to at least 12 contiguous bases of SEQ ID NO:37.

10. The method of claim 1, wherein the oligonucleotide is complementary to at least 15 contiguous bases of SEQ ID NO:37.

11. The method of claim 1, wherein the oligonucleotide is composed of 15 to 22 subunits and is 100% complementary to SEQ ID NO:37.

12. The method of claim 2, wherein X is alkyl amino of the form $NR_2$, where R is methyl, and where the phosphorodiamidate linkages containing piperazine groups are represented by the same structure, but where X is 1-piperazino.

* * * * *

SEQUENCE LISTING

<160> NUMBER OF SEQ ID NOS: 43

<210> SEQ ID NO 1
<211> LENGTH: 20
<212> TYPE: DNA
<213> ORGANISM: Poliovirus Mahoney strain

<400> SEQUENCE: 1
gtatcataat gggtgctcag                           20

<210> SEQ ID NO 2
<211> LENGTH: 20
<212> TYPE: DNA
<213> ORGANISM: Poliovirus Sabin strain

<400> SEQUENCE: 2
gtatcataat gggtgctcag                           20

<210> SEQ ID NO 3
<211> LENGTH: 24
<212> TYPE: DNA
<213> ORGANISM: Hepatitis A virus

<400> SEQUENCE: 3
aataatgaac atgtctagac aagg                      24

<210> SEQ ID NO 4
<211> LENGTH: 20
<212> TYPE: DNA
<213> ORGANISM: Rhinovirus 14

<400> SEQUENCE: 4
ctgtgatcat gggcgctcag                           20

<210> SEQ ID NO 5
<211> LENGTH: 20
<212> TYPE: DNA
<213> ORGANISM: Rhinovirus 16

<400> SEQUENCE: 5
ttgttatcat gggcgctcaa                           20

<210> SEQ ID NO 6
<211> LENGTH: 20
<212> TYPE: DNA
<213> ORGANISM: Rhinovirus 1B

<400> SEQUENCE: 6
ttggcatcat gggtgcccag                           20

<210> SEQ ID NO 7
<211> LENGTH: 22
<212> TYPE: DNA
<213> ORGANISM: Aphthovirus

<400> SEQUENCE: 7
caatgagcac aactgactgt tt                        22

<210> SEQ ID NO 8
<211> LENGTH: 26
<212> TYPE: DNA
<213> ORGANISM: Aphthovirus

<400> SEQUENCE:

```
gaccctatga atacaactga ctgttt                                            26

<210> SEQ ID NO 9
<211> LENGTH: 20
<212> TYPE: DNA
<213> ORGANISM: Coxsackievirus

<400> SEQUENCE: 9
caacaaaatg ggggctcaag                                                   20

<210> SEQ ID NO 10
<211> LENGTH: 34
<212> TYPE: DNA
<213> ORGANISM: Vesivirus (Pan-1)

<400> SEQUENCE: 10
gtaaatgaga atttgagcta tggctcaaac gctc                                   34

<210> SEQ ID NO 11
<211> LENGTH: 20
<212> TYPE: DNA
<213> ORGANISM: Porcine enteric calicivirus

<400> SEQUENCE: 11
cgtgatggct aattgccgtc                                                   20

<210> SEQ ID NO 12
<211> LENGTH: 19
<212> TYPE: DNA
<213> ORGANISM: Norwalk virus

<400> SEQUENCE: 12
gtgaatgatg atggcgtcg                                                    19

<210> SEQ ID NO 13
<211> LENGTH: 24
<212> TYPE: DNA
<213> ORGANISM: Hepatitis E virus

<400> SEQUENCE: 13
tggaggccca tcagtttatt aagg                                              24

<210> SEQ ID NO 14
<211> LENGTH: 18
<212> TYPE: DNA
<213> ORGANISM: Hepatitis C virus

<400> SEQUENCE: 14
gccatggagg cccatcag                                                     18

<210> SEQ ID NO 15
<211> LENGTH: 19
<212> TYPE: DNA
<213> ORGANISM: Artificial Sequence
<220> FEATURE:
<223> OTHER INFORMATION: synthetic antisense oligomer

<400> SEQUENCE: 15
gaccgtgcac catgagcac                                                    19

<210> SEQ ID NO 16
<211> LENGTH: 21
<212> TYPE: DNA
```

```
<213> ORGANISM: Artificial Sequence
<220> FEATURE:
<223> OTHER INFORMATION: synthetic antisense oligomer

<400> SEQUENCE: 16
cctgagcacc cattatgata c                                      21

<210> SEQ ID NO 17
<211> LENGTH: 24
<212> TYPE: DNA
<213> ORGANISM: Artificial Sequence
<220> FEATURE:
<223> OTHER INFORMATION: synthetic antisense oligomer

<400> SEQUENCE: 17
ccttgtctag acatgttcat tatt                                   24

<210> SEQ ID NO 18
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 18
ctgagcgccc atgatcacag                                        20

<210> SEQ ID NO 19
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 19
ttgagcgccc atgataacaa                                        20

<210> SEQ ID NO 20
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 20
ctgggcaccc atgatgccaa                                        20

<210> SEQ ID NO 21
<211> LENGTH: 22
<212> TYPE: DNA
<213> ORGANISM: Artificial Sequence
<220> FEATURE:
<223> OTHER INFORMATION: synthetic antisense oligomer

<400> SEQUENCE: 21
aaacagtcag ttgtgctcat tg                                     22

<210> SEQ ID NO 22
<211> LENGTH: 22
<212> TYPE: DNA
<213> ORGANISM: Artificial Sequence
<220> FEATURE:
<223> OTHER INFORMATION: synthetic antisense oligomer

<400> SEQUENCE: 22
aaacagtcag ttgtattcat ag                                     22
```

<210> SEQ ID NO 23
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 23
cttgagctcc cattttgctg                                           20

<210> SEQ ID NO 24
<211> LENGTH: 21
<212> TYPE: DNA
<213> ORGANISM: Artificial Sequence
<220> FEATURE:
<223> OTHER INFORMATION: synthetic antisense oligomer

<400> SEQUENCE: 24
cttgagcccc catttttgtt g                                         21

<210> SEQ ID NO 25
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 25
cctgtgctcc catcttgatg                                           20

<210> SEQ ID NO 26
<211> LENGTH: 30
<212> TYPE: DNA
<213> ORGANISM: Artificial Sequence
<220> FEATURE:
<223> OTHER INFORMATION: synthetic antisense oligomer

<400> SEQUENCE: 26
tgggtgggat caacccacag gctgttttaa                                30

<210> SEQ ID NO 27
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 27
gagccatagc tcaaattctc                                           20

<210> SEQ ID NO 28
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 28
tagctcaaat tctcatttac                                           20

<210> SEQ ID NO 29
<211> LENGTH: 20
<212> TYPE: DNA
<213> ORGANISM: Artificial Sequence
<220> FEATURE:

<223> OTHER INFORMATION: synthetic antisense oligomer

<400> SEQUENCE: 29
gagcgtttga gccatagctc                                          20

<210> SEQ ID NO 30
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 30
gacggcaatt agccatcacg                                          20

<210> SEQ ID NO 31
<211> LENGTH: 19
<212> TYPE: DNA
<213> ORGANISM: Artificial Sequence
<220> FEATURE:
<223> OTHER INFORMATION: synthetic antisense oligomer

<400> SEQUENCE: 31
cgacgccatc atcattcac                                           19

<210> SEQ ID NO 32
<211> LENGTH: 21
<212> TYPE: DNA
<213> ORGANISM: Artificial Sequence
<220> FEATURE:
<223> OTHER INFORMATION: synthetic antisense oligomer

<400> SEQUENCE: 32
cagagtttga gacattgtct c                                        21

<210> SEQ ID NO 33
<211> LENGTH: 23
<212> TYPE: DNA
<213> ORGANISM: Artificial Sequence
<220> FEATURE:
<223> OTHER INFORMATION: synthetic antisense oligomer

<400> SEQUENCE: 33
ccttaataaa ctgatgggcc tcc                                      23

<210> SEQ ID NO 34
<211> LENGTH: 18
<212> TYPE: DNA
<213> ORGANISM: Artificial Sequence
<220> FEATURE:
<223> OTHER INFORMATION: synthetic antisense oligomer

<400> SEQUENCE: 34
ctgatgggcc tccatggc                                            18

<210> SEQ ID NO 35
<211> LENGTH: 19
<212> TYPE: DNA
<213> ORGANISM: Artificial Sequence
<220> FEATURE:
<223> OTHER INFORMATION: synthetic antisense oligomer

<400> SEQUENCE: 35
gtgctcatgg tgcacggtc                                           19

```
<210> SEQ ID NO 36
<211> LENGTH: 19
<212> TYPE: DNA
<213> ORGANISM: Artificial Sequence
<220> FEATURE:
<223> OTHER INFORMATION: scrambled control sequence

<400> SEQUENCE: 36
gacatatcta atcatatac                                                  19

<210> SEQ ID NO 37
<211> LENGTH: 125
<212> TYPE: DNA
<213> ORGANISM: Hepatitis C virus

<400> SEQUENCE: 37
aagactgcta gccgagtagt gttgggtcgc gaaaggcctt gtggtactgc ctgatagggt      60
gcttgcgagt gccccgggag gtctcgtaga ccgtgcacca tgagcacgaa tcctaaacct     120
caaag                                                                125

<210> SEQ ID NO 38
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 38
ggcctttcgc gacccaacac                                                 20

<210> SEQ ID NO 39
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 39
atcaggcagt accacaaggc                                                 20

<210> SEQ ID NO 40
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 40
cacggtctac gagacctccc                                                 20

<210> SEQ ID NO 41
<211> LENGTH: 13
<212> TYPE: PRT
<213> ORGANISM: Artificial Sequence
<220> FEATURE:
<223> OTHER INFORMATION: synthetic Arginine-rich peptide
<220> FEATURE:
<221> NAME/KEY: misc_feature
<222> LOCATION: (12)..(12)
<223> OTHER INFORMATION: Xaa = 6-aminohexanoic acid
<220> FEATURE:
<221> NAME/KEY: misc_feature
<222> LOCATION: (13)..(13)
<223> OTHER INFORMATION: Xaa = beta-Alanine

<400> SEQUENCE: 41
```

```
Arg Arg Arg Arg Arg Arg Arg Arg Phe Phe Xaa Xaa
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (5)..(5)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (11)..(11)
<223> OTHER INFORMATION: Xaa = 6-aminohexanoic acid
<220> FEATURE:
<221> NAME/KEY: misc_feature
<222> LOCATION: (13)..(13)
<223> OTHER INFORMATION: Xaa = 6-aminohexanoic acid
<220> FEATURE:
<221> NAME/KEY: misc_feature
<222> LOCATION: (14)..(14)
<223> OTHER INFORMATION: Xaa = beta-Alanine

<400> SEQUENCE: 42

```
Arg Xaa Arg Arg Xaa Arg Arg Xaa Arg Arg Xaa Arg Xaa Xaa
1               5                   10
```

<210> SEQ ID NO 43
<211> LENGTH: 17
<212> TYPE: PRT
<213> ORGANISM: Artificial Sequence
<220> FEATURE:
<223> OTHER INFORMATION: synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (4)..(4)
<223> OTHER INFORMATION: Xaa = 6-aminohexanoic acid
<220> FEATURE:
<221> NAME/KEY: misc_feature
<222> LOCATION: (6)..(6)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (10)..(10)
<223> OTHER INFORMATION: Xaa = 6-aminohexanoic acid
<220> FEATURE:
<221> NAME/KEY: misc_feature
<222> LOCATION: (12)..(12)
<223> OTHER INFORMATION: Xaa = 6-aminohexanoic acid
<220> FEATURE:
<221> NAME/KEY: misc_feature
<222> LOCATION: (14)..(14)
<223> OTHER INFORMATION: Xaa = 6-aminohexanoic acid
<220> FEATURE:
<221> NAME/KEY: misc_feature
<222> LOCATION: (16)..(16)
<223> OTHER INFORMATION: Xaa = 6-aminohexanoic acid

```
<220> FEATURE:
<221> NAME/KEY: misc_feature
<222> LOCATION: (17)..(17)
<223> OTHER INFORMATION: Xaa = beta-Alanine

<400> SEQUENCE: 43

Arg Xaa Arg Xaa Arg Xaa Arg Xaa Arg Xaa Arg Xaa Arg Xaa Arg Xaa
1               5                   10                  15

Xaa
```